United States Patent [19]
Amano et al.

[11] Patent Number: 6,030,342
[45] Date of Patent: Feb. 29, 2000

[54] DEVICE FOR MEASURING CALORIE EXPENDITURE AND DEVICE FOR MEASURING BODY TEMPERATURE

[75] Inventors: Kazuhiko Amano, Suwa; Kazuo Uebaba, Yokohama; Hitoshi Ishiyama, Toride, all of Japan

[73] Assignee: Seiko Epson Corporation, Tokyo, Japan

[21] Appl. No.: 09/011,554

[22] PCT Filed: Jun. 12, 1997

[86] PCT No.: PCT/JP97/02029

§ 371 Date: Feb. 9, 1998

§ 102(e) Date: Feb. 9, 1998

[87] PCT Pub. No.: WO97/47239

PCT Pub. Date: Dec. 18, 1997

[30] Foreign Application Priority Data

Jun. 12, 1996 [JP] Japan .................................... 8-151378
Nov. 20, 1996 [JP] Japan .................................... 8-309749
May 16, 1997 [JP] Japan .................................... 9-127648

[51] Int. Cl.$^7$ .................................. A61B 5/02; A61B 5/00
[52] U.S. Cl. ......................... 600/301; 600/500; 600/503; 600/549; 702/131
[58] Field of Search .................................. 600/483, 485, 600/500, 502, 503, 300, 301, 481, 549; 702/130, 131

[56] References Cited

U.S. PATENT DOCUMENTS 4,090,504  5/1978  Nathan ..................................... 600/483
5,509,422  4/1996  Fukami ..................................... 600/483
5,515,858  5/1996  Myllymaki ............................... 600/483

FOREIGN PATENT DOCUMENTS

| | | |
|---|---|---|
| 54-62878 | 5/1979 | Japan . |
| 2-80029 | 3/1990 | Japan . |
| 4-253839 | 9/1992 | Japan . |
| 6-10144 | 1/1994 | Japan . |
| 6-142087 | 5/1994 | Japan . |
| 8-52119 | 2/1996 | Japan . |
| 8-80287 | 3/1996 | Japan . |
| 8-126632 | 5/1996 | Japan . |
| 8-131425 | 5/1996 | Japan . |

*Primary Examiner*—Cary O'Connor
*Assistant Examiner*—Navin Natnithithadha
*Attorney, Agent, or Firm*—Eric B. Janofsky

[57] ABSTRACT

In order to obtain calorie expenditure with good accuracy, the device is provided with a basal metabolic state specifying element (142) which specifies the subject's basal metabolic state from his body temperature; a correlation storing element (151) which stores respective regression formulas showing the correlation between the pulse rate and the calorie expenditure when the subject is at rest or active; a correlation correcting element (152) which correcting the stored regression formulas using the basal metabolic state; a body motion determining element (104) which determines whether or not the subject is at rest; and a regression formula selecting element (153) which selects the regression formula which should be used in accordance with the results of this determination. The subject's pulse rate is applied in the selected regression formula, and the calorie expenditure corresponding to this pulse rate is calculated by calorie expenditure calculator (162).

36 Claims, 34 Drawing Sheets

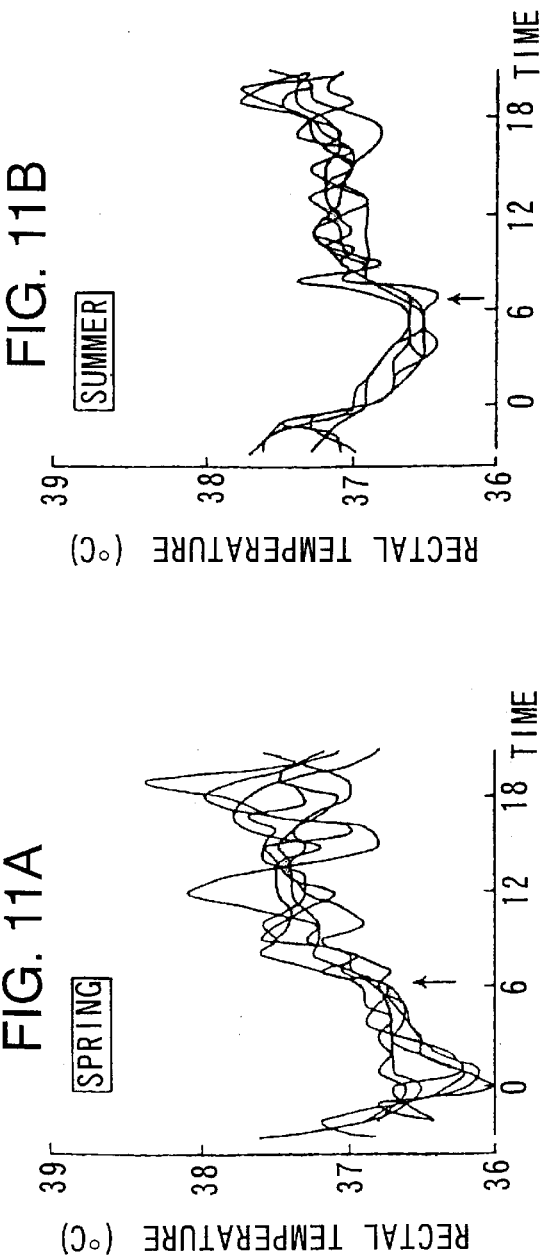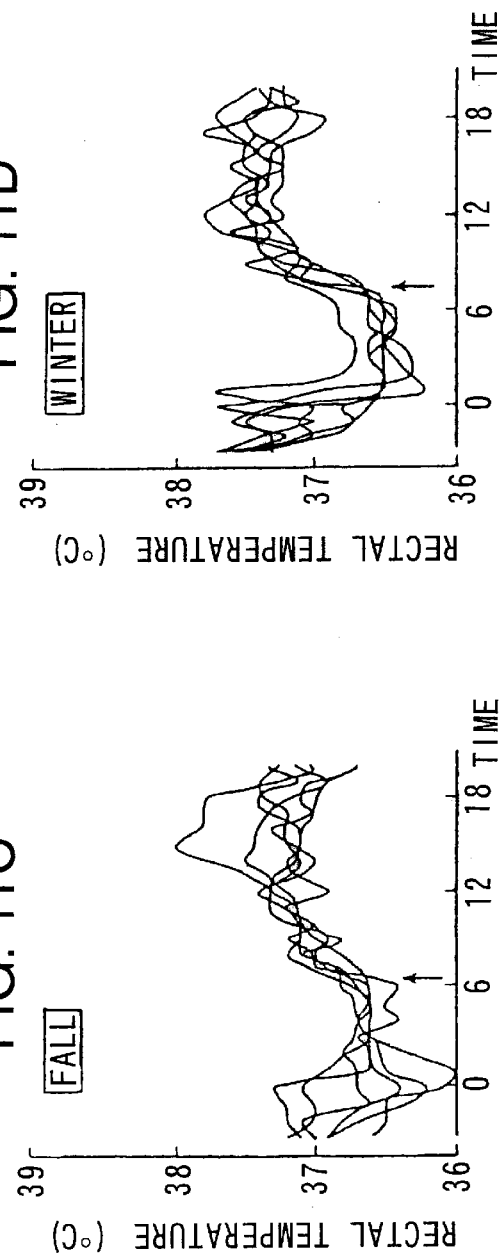

FIG. 12

| STANDARD BASAL METABOLIC VALUES PER UNIT BODY AREA (kcal/$m^2$/hour) | | |
|---|---|---|
| AGE (years) | MALE | FEMALE |
| 0 ~ | 48.7 | 48.4 |
| 1 ~ | 53.6 | 52.6 |
| 2 ~ | 56.2 | 55.1 |
| 3 ~ | 57.2 | 55.6 |
| 4 ~ | 56.5 | 54.0 |
| 5 ~ | 55.1 | 51.6 |
| 6 ~ | 52.9 | 49.5 |
| 7 ~ | 51.1 | 47.6 |
| 8 ~ | 49.3 | 46.2 |
| 9 ~ | 47.5 | 44.8 |
| 10 ~ | 46.2 | 44.1 |
| 11 ~ | 45.3 | 43.1 |
| 12 ~ | 44.5 | 42.2 |
| 13 ~ | 43.5 | 41.2 |
| 14 ~ | 42.8 | 39.8 |
| 15 ~ | 41.7 | 38.1 |
| 16 ~ | 41.0 | 36.9 |
| 17 ~ | 40.3 | 36.0 |
| 18 ~ | 39.6 | 35.6 |
| 19 ~ | 38.8 | 35.1 |
| 20 ~ 29 | 37.5 | 34.3 |
| 30 ~ 39 | 36.5 | 33.2 |
| 40 ~ 49 | 35.6 | 32.5 |
| 50 ~ 59 | 34.8 | 32.0 |
| 60 ~ 64 | 34.0 | 31.6 |
| 65 ~ 69 | 33.3 | 31.4 |
| 70 ~ 74 | 32.6 | 31.1 |
| 75 ~ 79 | 31.9 | 30.9 |
| 80 ~ | 30.7 | 30.0 |

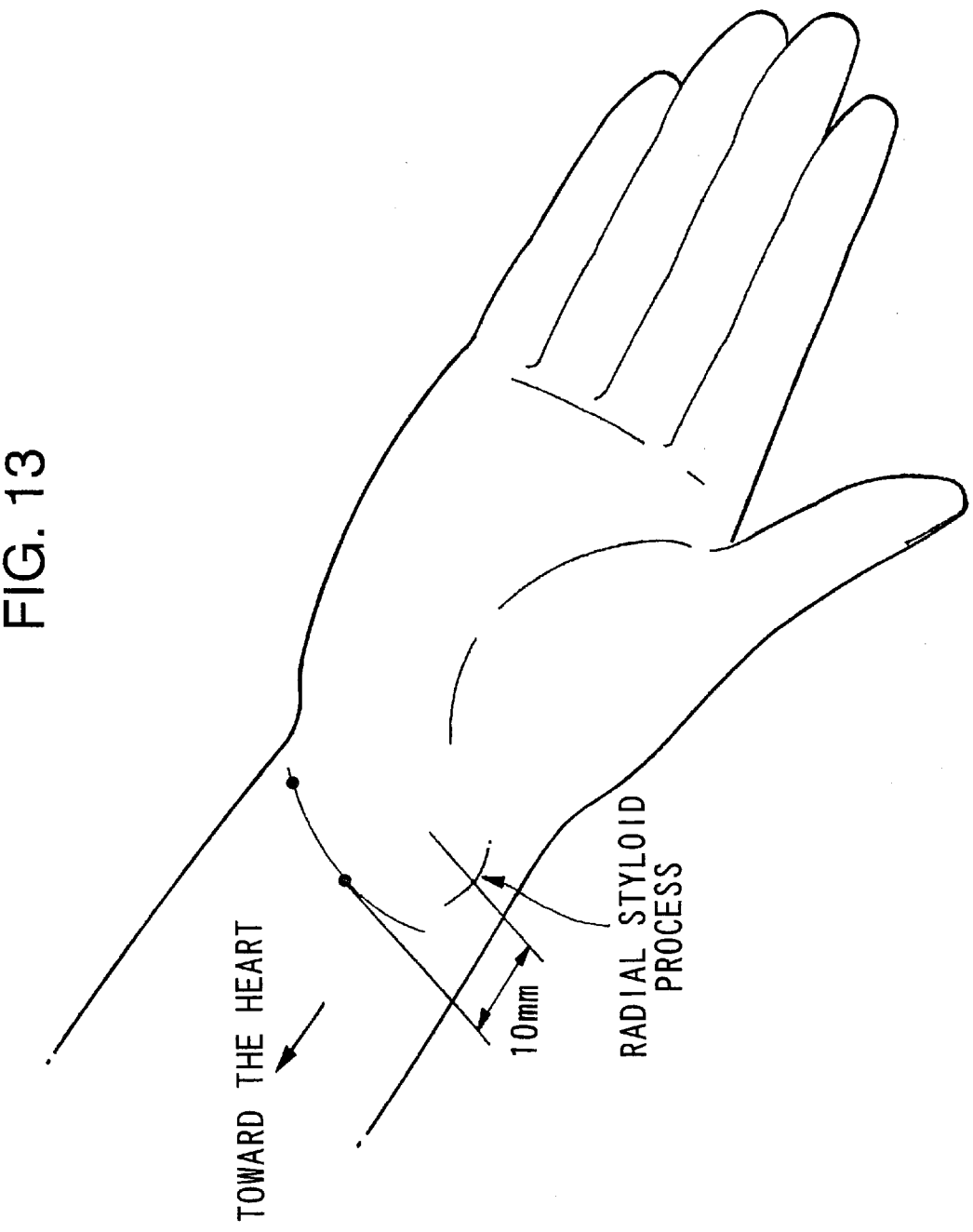

WHEN DRY

AFTER IMMERSING IN WATER

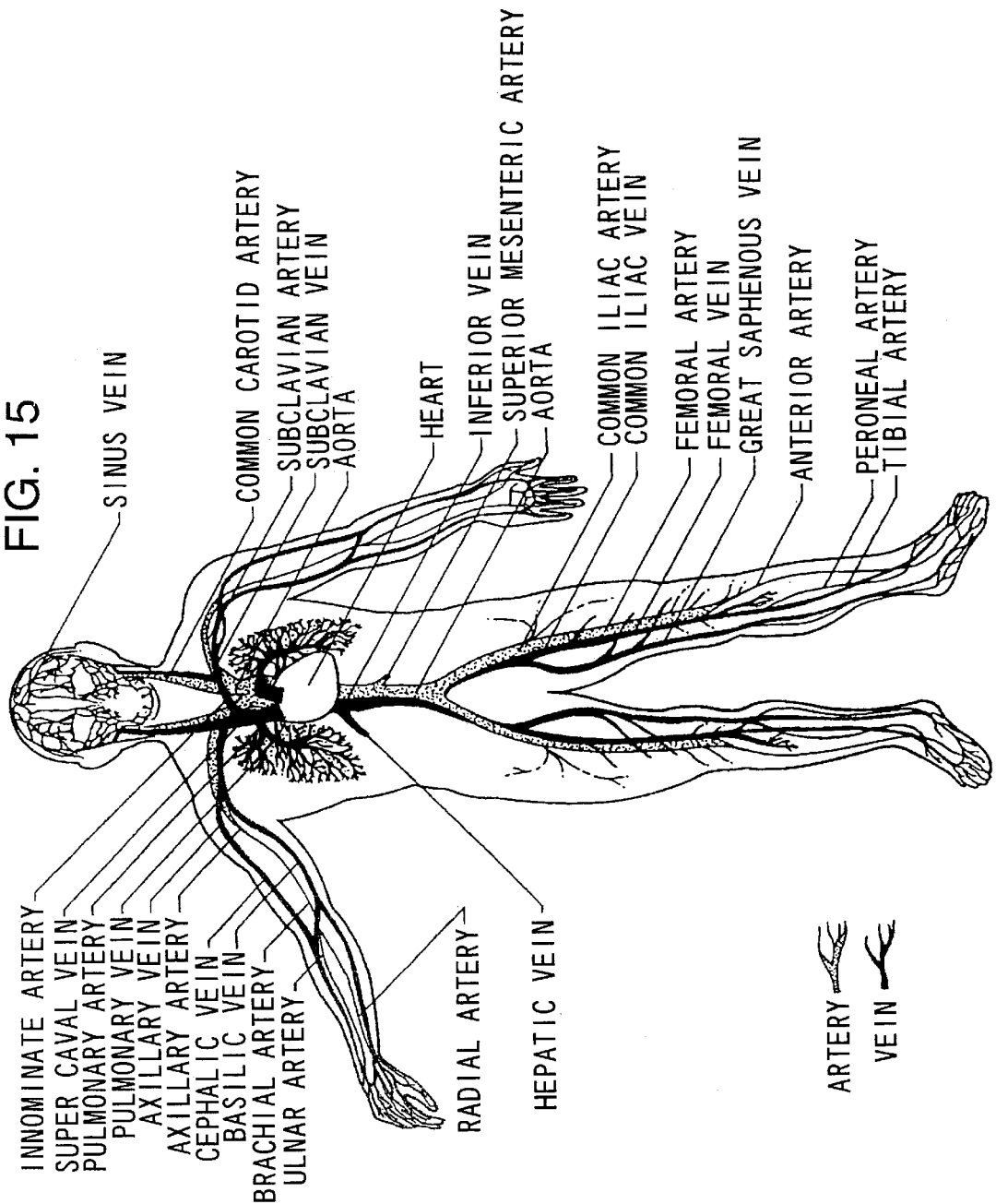

205: DISPLAY

FIG. 22
| ACHIEVEMENT RATE G | FACE CHART |
|---|---|
| $G < 70$ |  |
| $70 \leqq G < 80$ |  |
| $80 \leqq G < 90$ |  |
| $90 \leqq G < 100$ | 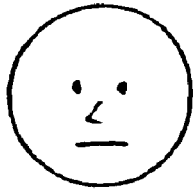 |
| $100 \leqq G < 110$ |  |
| $110 \leqq G$ |  |

| | | | | | | | | |
|---|---|---|---|---|---|---|---|---|
| 4.0~3.5Hz | M18 | M28 | ⋯ | ⋯ | ⋯ | ⋯ | ⋯ | M88 |
| 3.5~3.0Hz | M17 | | | | | | ⋰ | ⋮ |
| 3.0~2.5Hz | M16 | | | | | ⋰ | | |
| 2.5~2.0Hz | M15 | | | | ⋰ | | | |
| 2.0~1.5Hz | M14 | | | ⋰ | | | | |
| 1.5~1.0Hz | M13 | | ⋰ | | | | | |
| 1.0~0.5Hz | M12 | M22 | | | | | | |
| 0.5~0.0Hz | M11 | M21 | M31 | M41 | M51 | M61 | M71 | M81 |

FIG. 30C

| | | | | | | | | |
|---|---|---|---|---|---|---|---|---|
| 4.0~3.5Hz | 10 | 8 | 5 | 0 | 0 | 0 | 0 | 0 |
| 3.5~3.0Hz | 5 | 4 | 2 | 0 | 0 | 0 | 0 | 0 |
| 3.0~2.5Hz | 2 | 1 | 1 | 0 | 0 | 0 | 0 | 0 |
| 2.5~2.0Hz | 2 | 1 | 3 | 0 | 0 | 0 | 0 | 0 |
| 2.0~1.5Hz | 2 | 2 | 2 | 1 | 0 | 0 | 0 | 0 |
| 1.5~1.0Hz | 6 | 5 | 5 | 4 | 4 | 4 | 4 | 4 |
| 1.0~0.5Hz | 0 | 1 | 1 | 1 | 1 | 1 | 1 | 1 |
| 0.5~0.0Hz | 0 | 1 | 1 | 3 | 3 | 3 | 3 | 3 |

FIG. 32
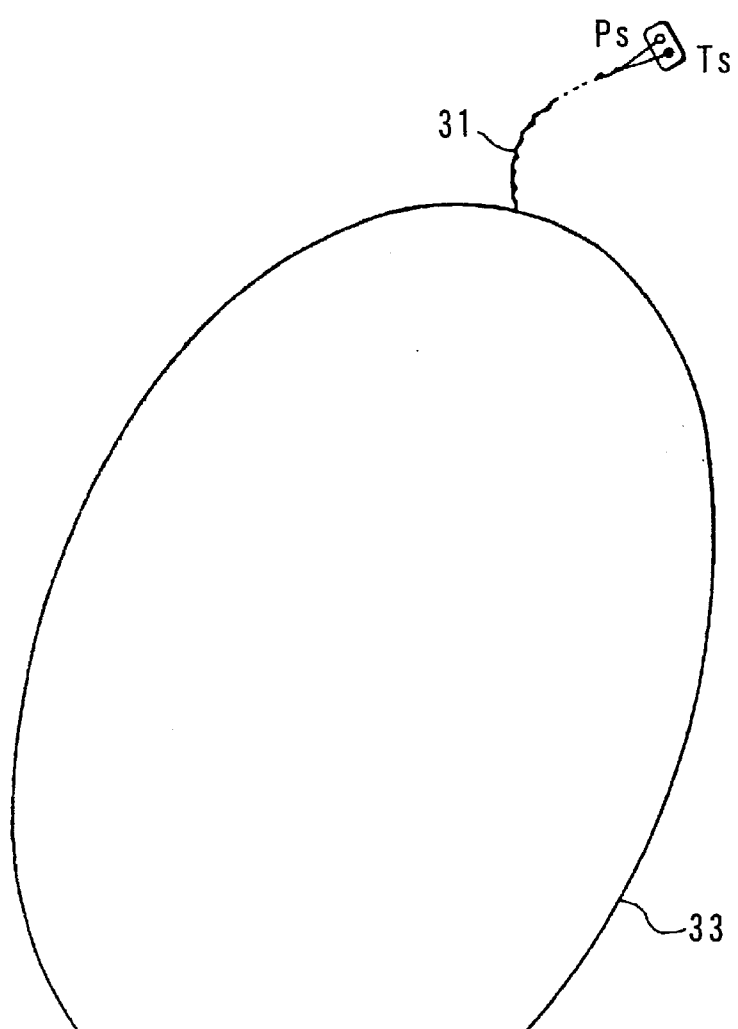
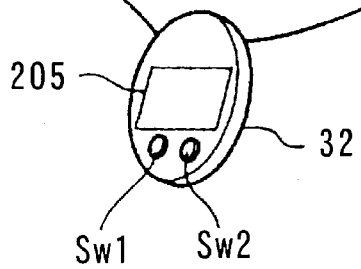
FIG. 33
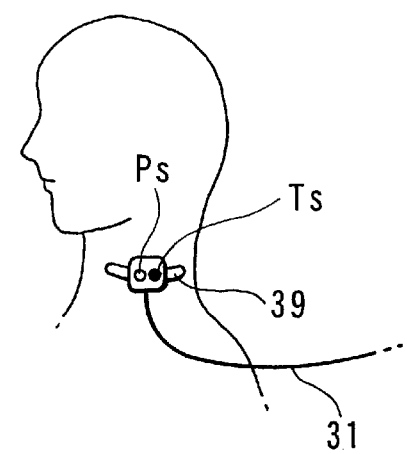

DEVICE FOR MEASURING CALORIE EXPENDITURE AND DEVICE FOR MEASURING BODY TEMPERATURE

TECHNICAL FIELD

The present invention relates to a calorie expenditure measuring device which can accurately measure the calorie expenditure by a subject regardless of whether the subject is resting or active, without being effected by such factors as the temperature of the surrounding environment, daily or annual fluctuations in the subject's physical state, this device accordingly being useful in maintaining health. The present invention is further related to a body temperature measuring device suitably employed in the aforementioned calorie expenditure measuring device which can continuously measure a body temperature which is as close as possible to the subject's deep body temperature, and is therefore also useful in maintaining health.

BACKGROUND ART

In this time of abundant food, calorie expenditure during exercise or daily activities has been recognized as one important index for maintaining health. Accordingly, the determination of calories expended is very significant. The standard total number of calories expended daily may vary widely, from a minimum of 1,000 kcal for a 1-year old child to a maximum of 3,800 Kcal for a 17-year teenager.

When measuring calorie expenditure, accuracy of within about 5% of the minimum value is considered necessary. Accordingly, the measurement error must be within 50 kcal.

Calorie expenditure measuring devices, such as th at disclosed in Japanese Patent Application Hei 8-52119 for example, has been proposed as devices for measuring the body's calorie expenditure. Such calorie expenditure measuring devices record the subject's sex, age, height, body weight, body fat ratio, and other constants in advance, as well as a table of standard basal metabolism values per unit of surface area on the body. These devices also use formulas for calculating the calorie expenditure when the subject is at rest or is exercising. When measuring the calorie expenditure, the measured pulse rate value and each of the constants cited above are substituted into formulas according to whether the subject is resting or exercising. Calorie expenditure is then calculated by referring to the aforementioned table of standard basal metabolism values.

However, the conventional devices for measuring calories expended described above have the following problems.

First, these conventional calorie expenditure measuring devices are provided with a comparison and determination device which determines the calculation formula to be used by comparing the measured pulse rat e and the "pulse rate threshold value (pulse rate when standing quietly)". However, it is well known that the pulse rate may rise due to various factors, including stress. Thus, since these devices determine the calculation formula which will be used according to the pulse rate only, they cannot discriminate between whether an increase in the pulse rate is due to factors other than increased activity, such as stress, or because the subject is actually exercising. As a result, calorie expenditure may be incorrectly calculated.

Second, in recent years it has come to be understood that there are a variety of physiological parameters, pulse rate included, that are subject to cyclical variation (daily, monthly or annually). For this reason, if the calculation of calorie expenditure is not corrected for this variation, then the accuracy of the calculation is suspect. Conventional calorie expenditure measuring devices do not take into consideration the fact that pulse rate varies cyclically, so that accurate measurement of calorie expenditure is difficult.

Thus, measurement accuracy of within 50 kcal as described above cannot be obtained using these conventional calorie expenditure measuring devices.

DISCLOSURE OF INVENTION

The present invention was conceived in consideration of the above-described circumstances, and has as its first objective the provision of a calorie expenditure measuring device which can accurately discriminate between resting and active states, and which can calculate the calorie expenditure with high accuracy by taking into consideration physical and psychological effects as well as cyclical variation in the pulse rate.

Further, the present invention has as its second objective the provision of a body temperature measuring device suitably employed in this calorie expenditure measuring device which continuously measures a body temperature which is as close as possible to the subject's deep body temperature.

In order to achieve the above stated first objective, the present invention is firstly characterized in the provision of a basal metabolic state specifying means for specifying the subject's basal metabolic state; a correlation recording means for recording the correlation between the pulse rate and calorie expenditure; a correlation correcting means for correcting the correlation stored in the correlation storing means by using the basal metabolic state specified by the basal metabolic state specifying means; and a calorie calculating means for applying the subject's pulse rate in the correlation stored in the correlation storing means, to calculate the calorie expenditure corresponding to this pulse rate.

In order to achieve the aforementioned second objective, the present invention is secondly characterized with the provision of a pulse wave detecting means for detecting over a specific range the pulse pressure around a site at which the subject's pulse is present; a temperature detecting means for detecting temperature, which is provided near the pulse wave detecting means; and a body temperature specifying means for specifying the temperature which was detected at the site at which the largest pulse pressure was detected from among the pulse pressures which were detected over the aforementioned specific region, as the body temperature.

As a result of the first characteristic described above, it is possible to calculate the calorie expenditure per unit time with excellent accuracy since the subject's psychological state, and of course his resting or active state, are taken into consideration. Further, it is also possible to more accurately determine calorie expenditure since monthly and annual fluctuations in the subject's state are taken into consideration.

Further, as a result of the above described second characteristic, the pulse pressure is detected over a specific area near where a pulse is present, and the temperature at the site where the pulse wave having the highest pressure within this area was detected is measured as the body temperature. As a result, it is possible to measure at the periphery a body temperature which is stable and is as close as possible to the deep body temperature. Moreover, once this measurement site is determined, continuous measurement is possible without any conscious recognition by the subject.

3B is a planar view thereof.

Figure 4A:
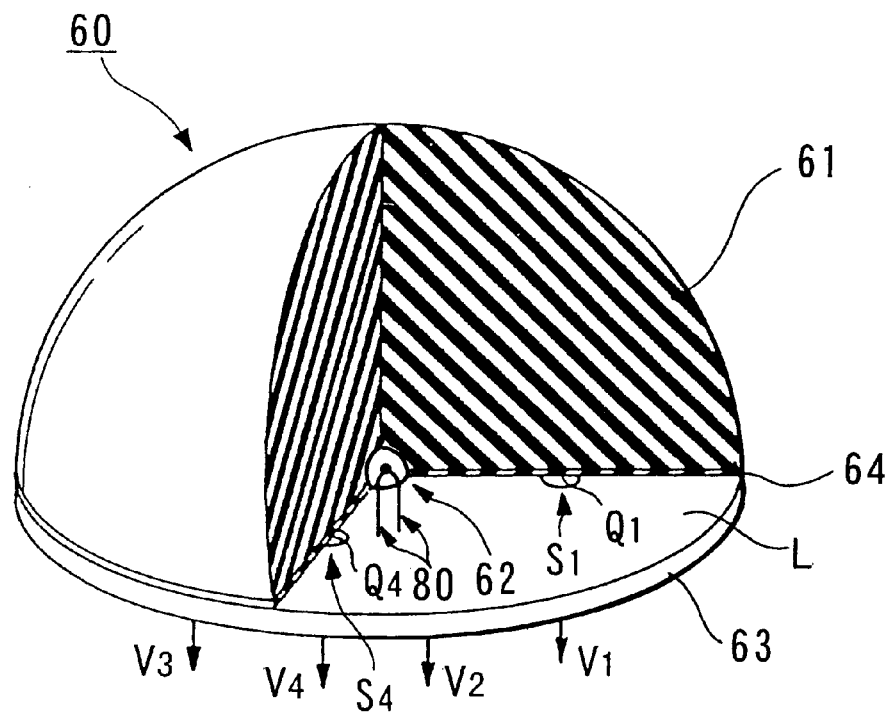
Figure 4B:
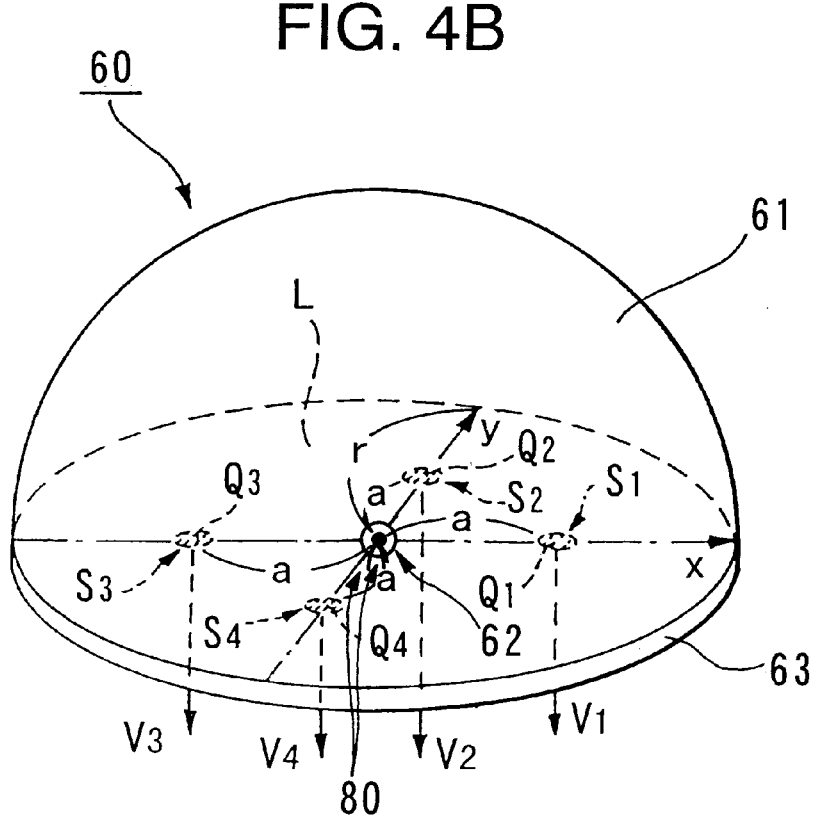

FIG. 4A is a partial cross-section perspective view of a portion of this device in cross-section showing the structure of the device's temperature sensor and pressure sensor;

FIG. 4B is a transparent perspective view of this part in cross-section.

Figure 5:
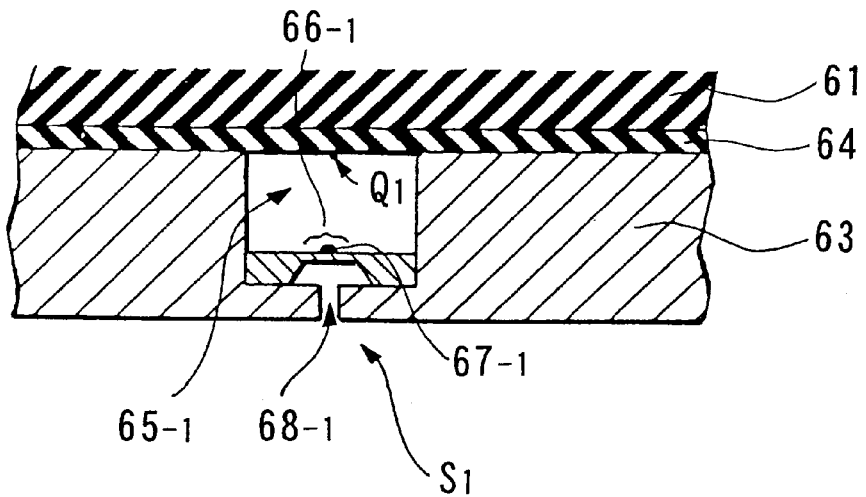

FIG. 5 is a cross-sectional view showing an enlargement of the connection between the elastic rubber in this pressure sensor and the semiconductor substrate.

Figure 6:
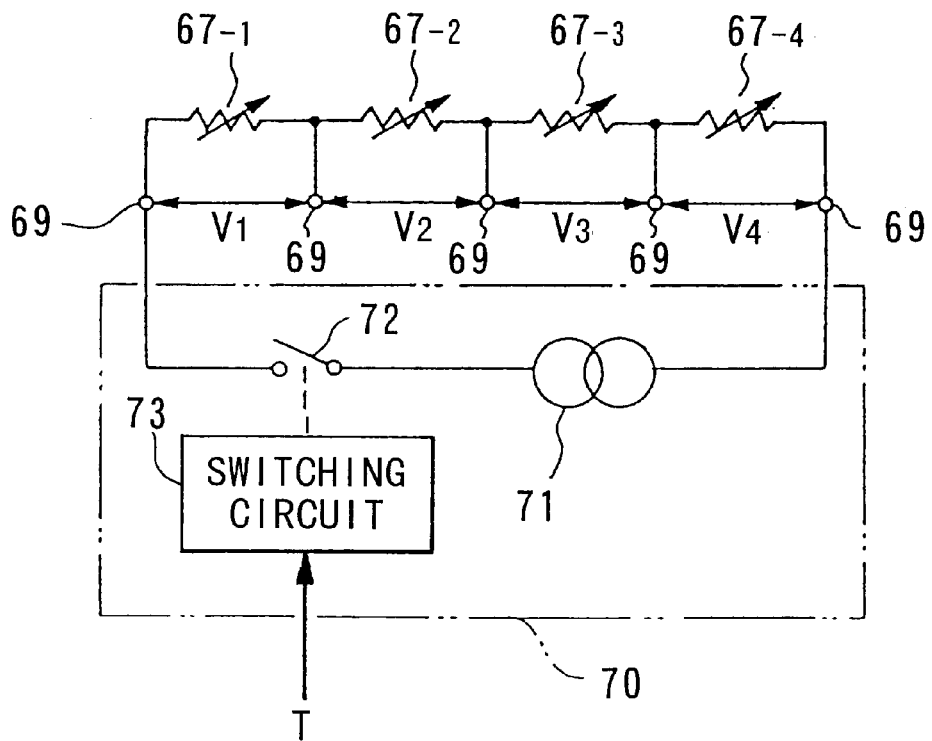

FIG. 6 is a block diagram showing a design in which a bias circuit has been added to the pressure sensor.

Figure 7:
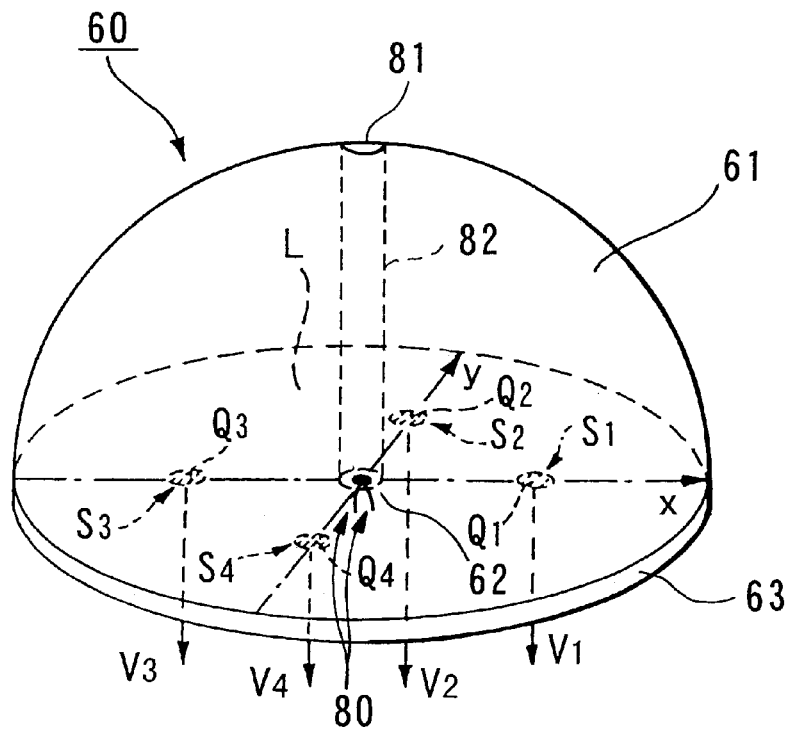

FIG. 7 is a slant transparent view of a portion in cross-section showing another structural example of the pressure sensor and temperature sensor.

Figure 8:
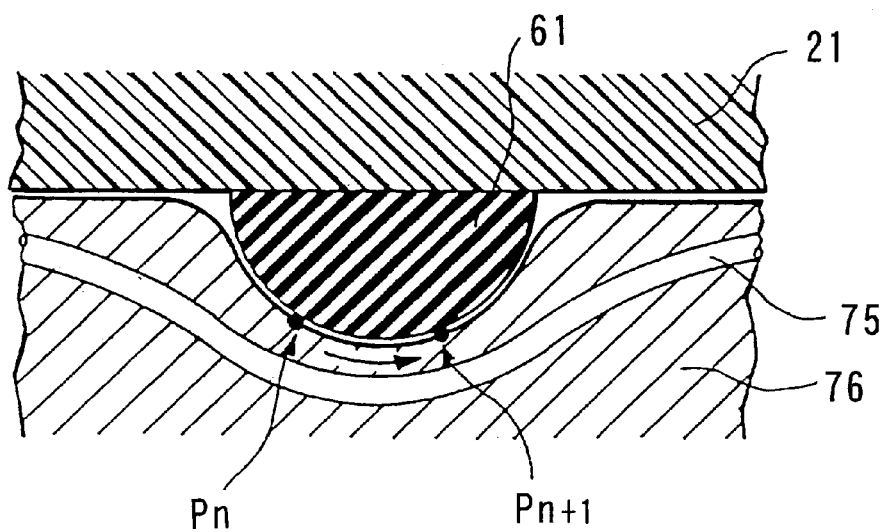

FIG. 8 is a view in cross-section of an essential component, provided for explaining the theory of pulse wave detection using this pressure sensor.

Figure 9:
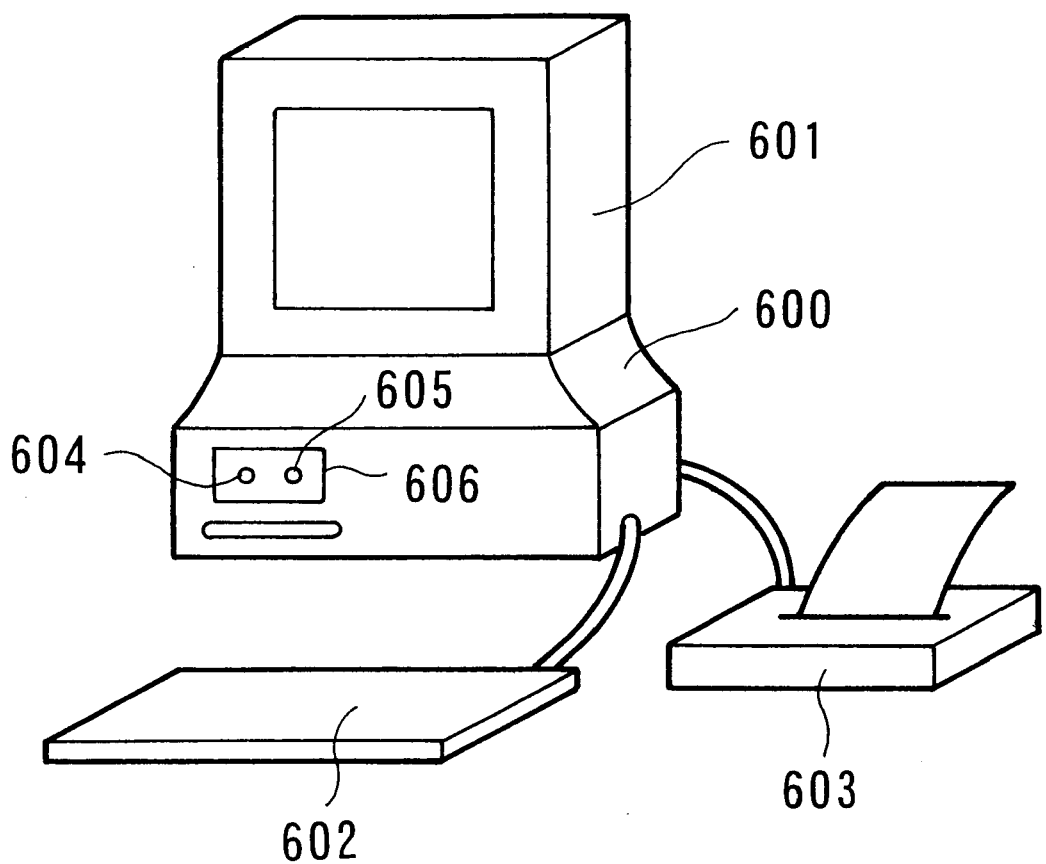

FIG. 9 is a diagram showing the structure of the external devices which carries out the sending and receiving of information with the device.

Figure 10A:
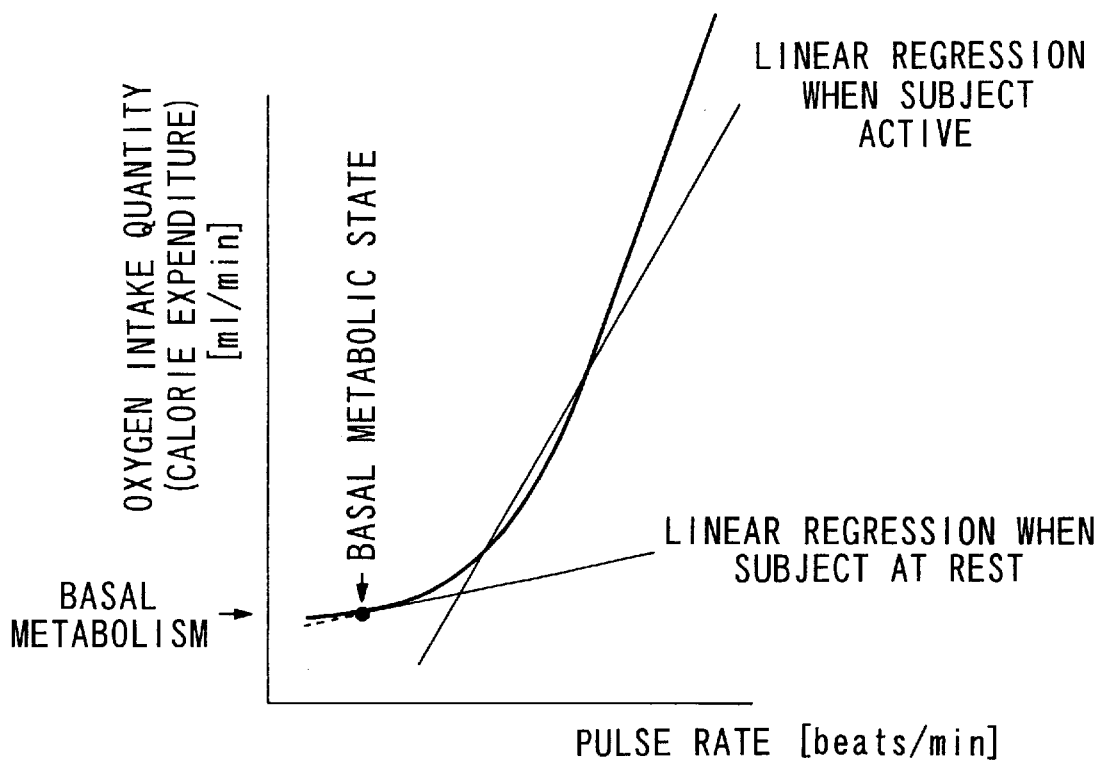
Figure 10B:
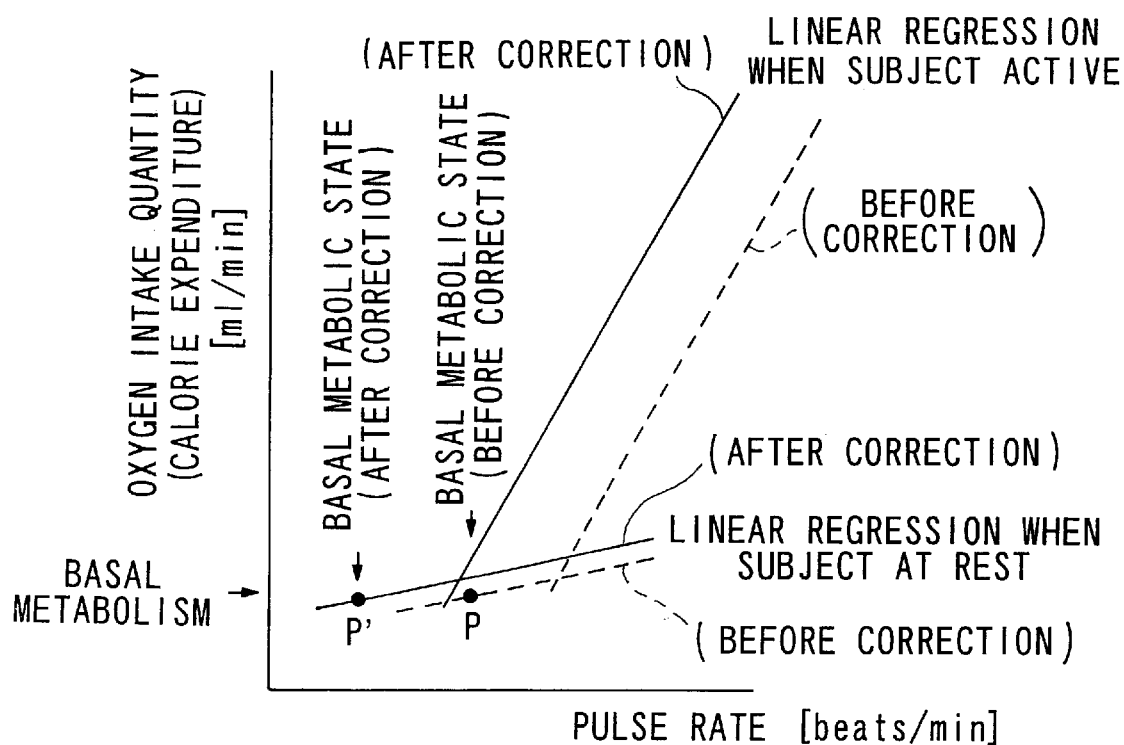

FIG. 10A shows the regression formulas for resting and active states which are used in the calculation of calorie expenditure in this device;

FIG. 10B is a diagram provided for explaining the correction of the regression formula in the device.

FIGS. 11A–11D are graphs showing the daily change in the rectal temperature in several individuals during the spring, summer, winter and fall, respectively.

FIG. 12 is a table showing the standard basal metabolic values per unit area of body determined separately according to age and sex.

FIG. 13 shows the external appearance of the site at which measurements are conducted in an experiment to measure body temperature in the embodiment of the present invention.

Figure 14A:
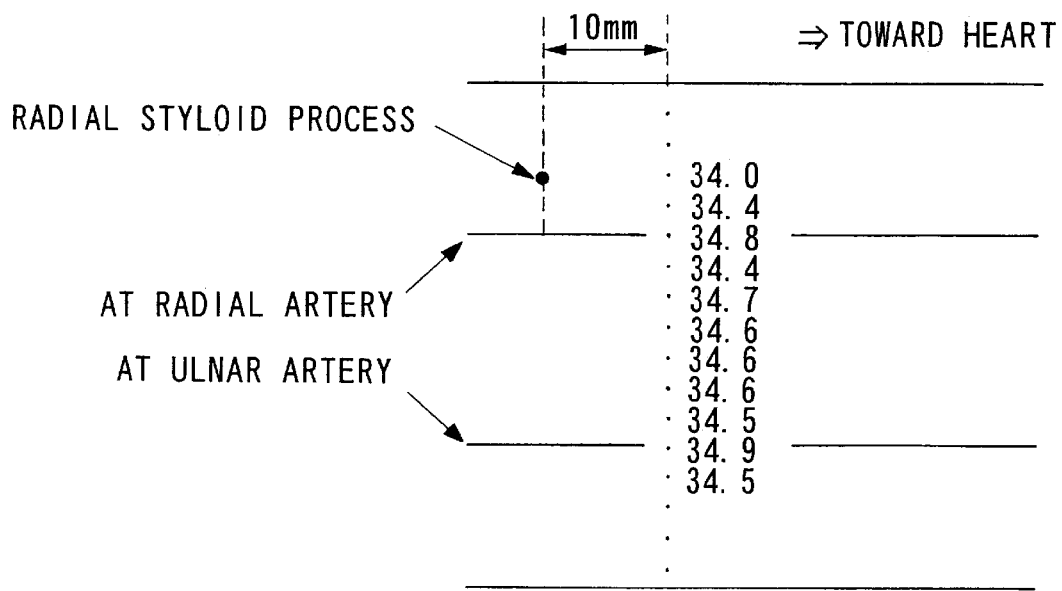
Figure 14B:
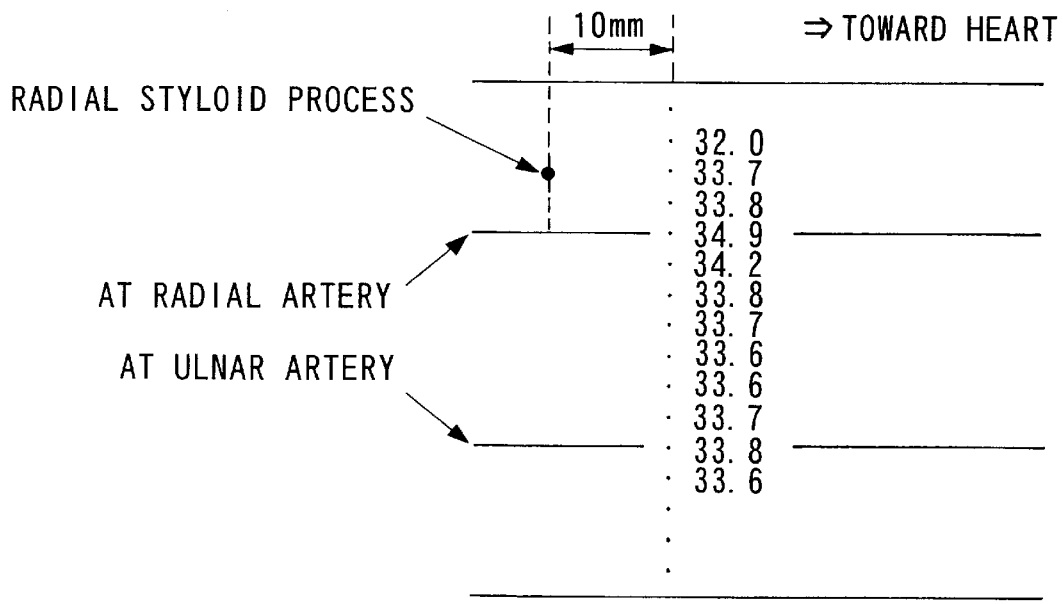

FIG. 14A is a diagram showing the positions at which measurements were made in this experiment, and the results of temperature measurements at each of these site, when the area was dry;

FIG. 14B shows these results after the area was immersed in water.

FIG. 15 is a diagram provided for explaining the broad circulatory system of the human body.

Figure 16:
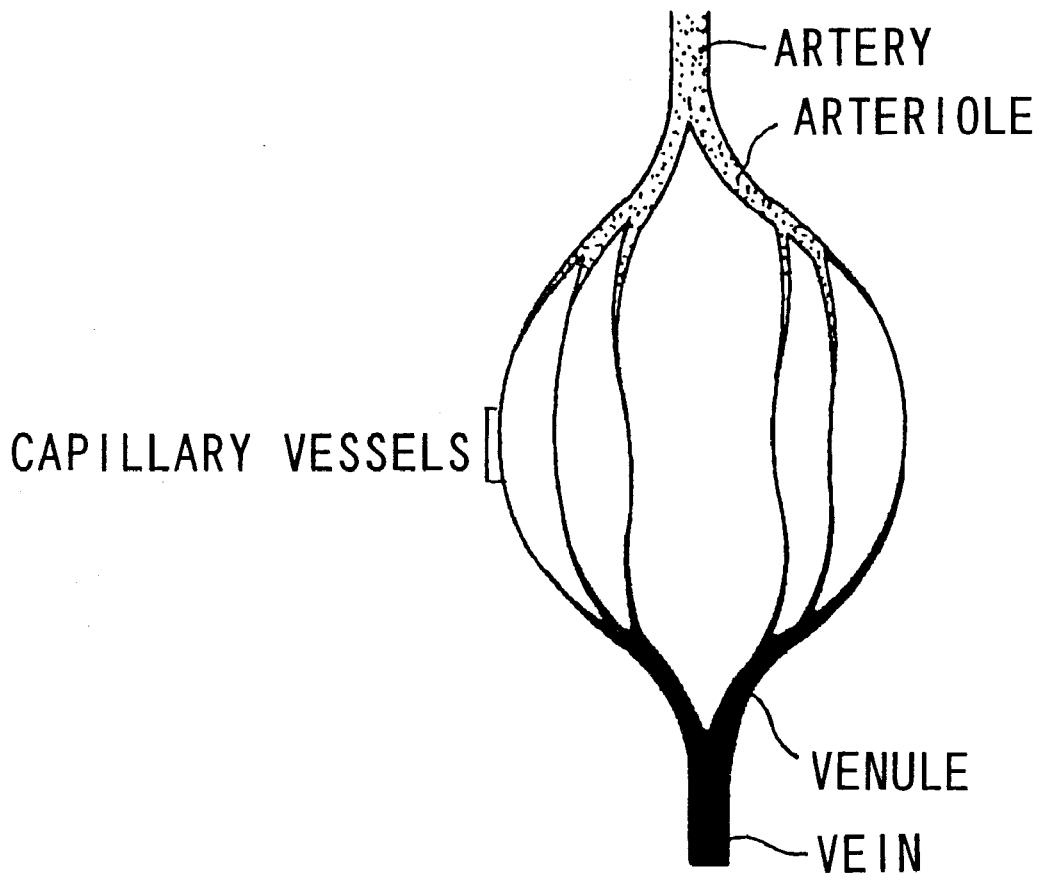

FIG. 16 is a diagram showing arterial and venous branching in the micro circulatory system of the human body.

Figure 17:
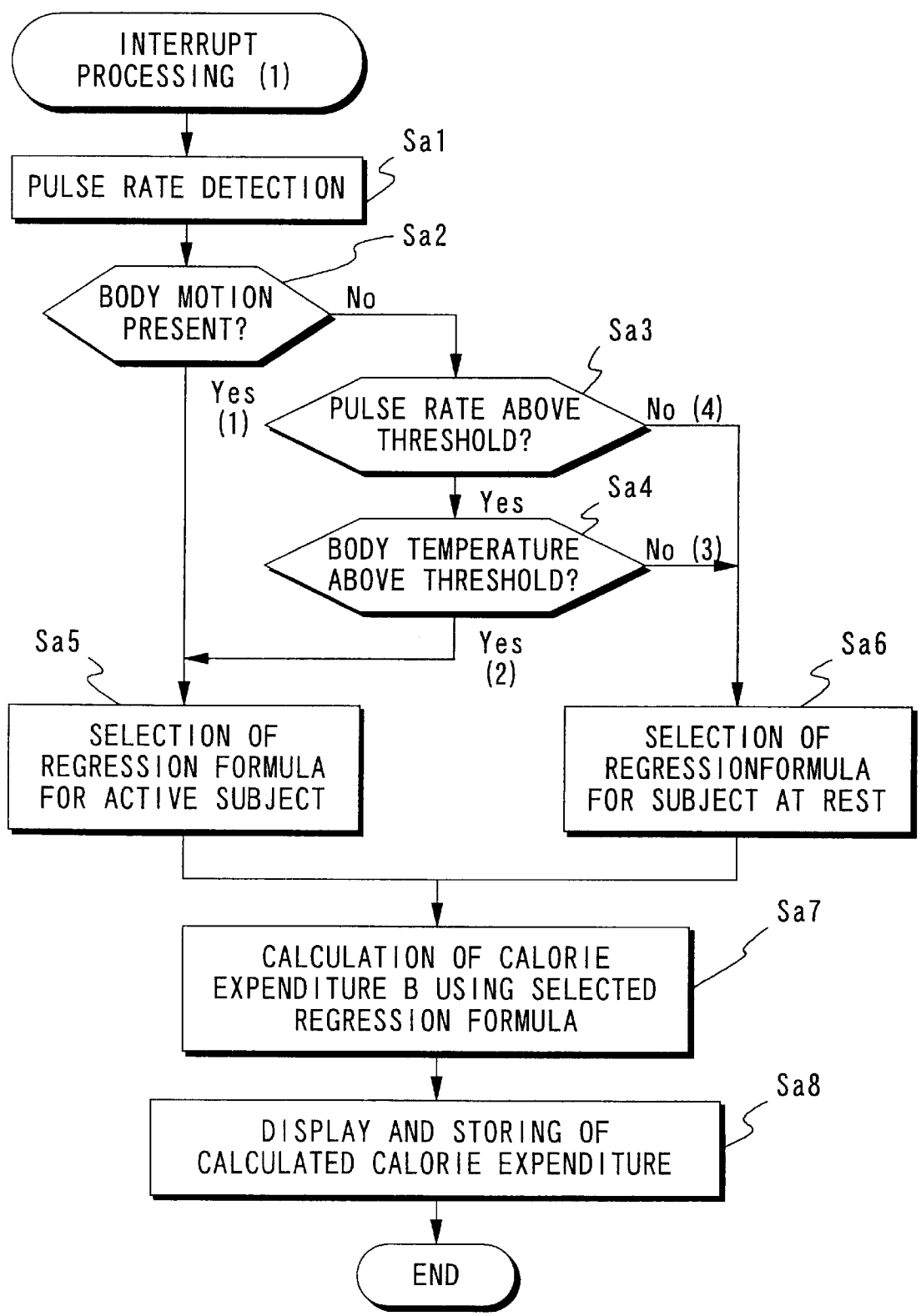

FIG. 17 is a flow chart showing the interrupt processing (1) which is carried out in this device.

Figure 18:
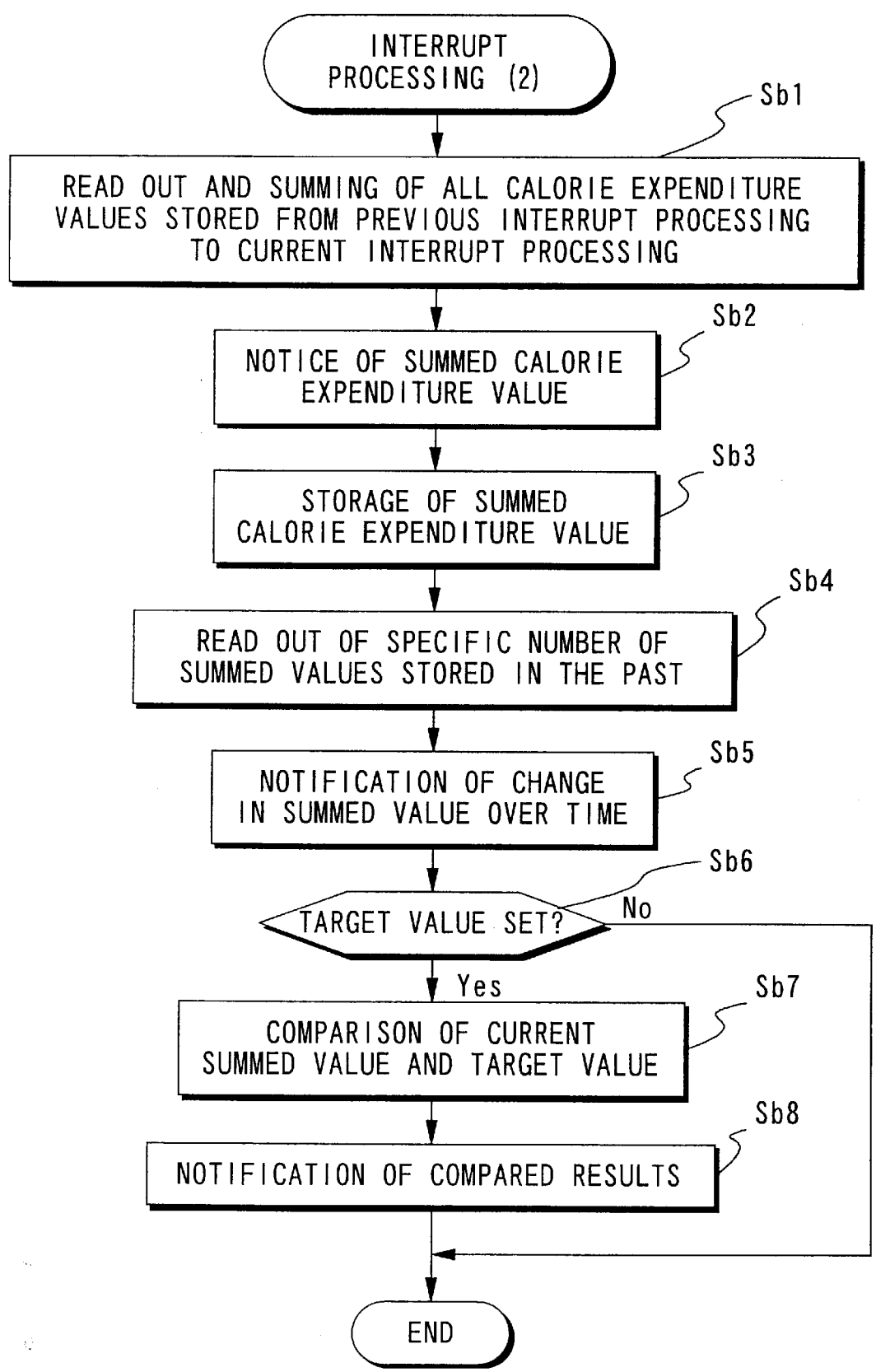

FIG. 18 is a flow chart showing the interrupt processing (2) which is carried out in this device.

Figure 19:
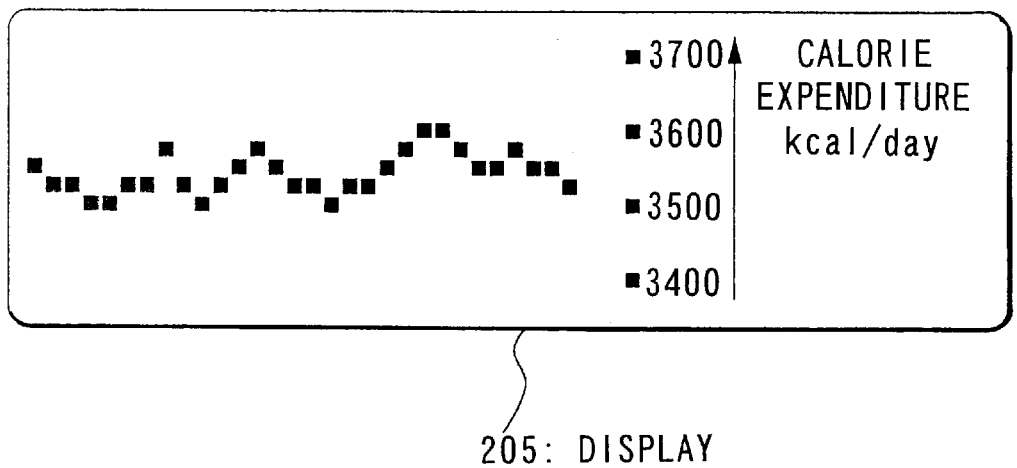

FIG. 19 is a diagram showing an example of the display in this device.

Figure 20:
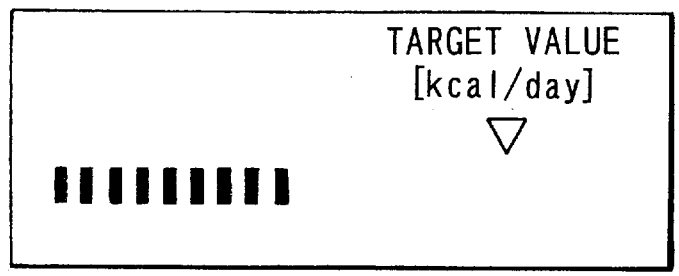

FIG. 20 is a diagram showing an example of the display in this device.

Figure 21:
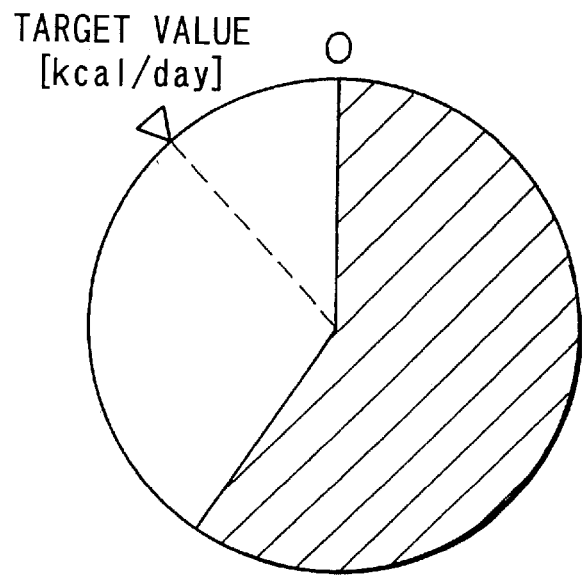

FIG. 21 is a diagram showing an example of the display in this device.

FIG. 22 is a diagram showing an example of the display in this device.

Figure 23:
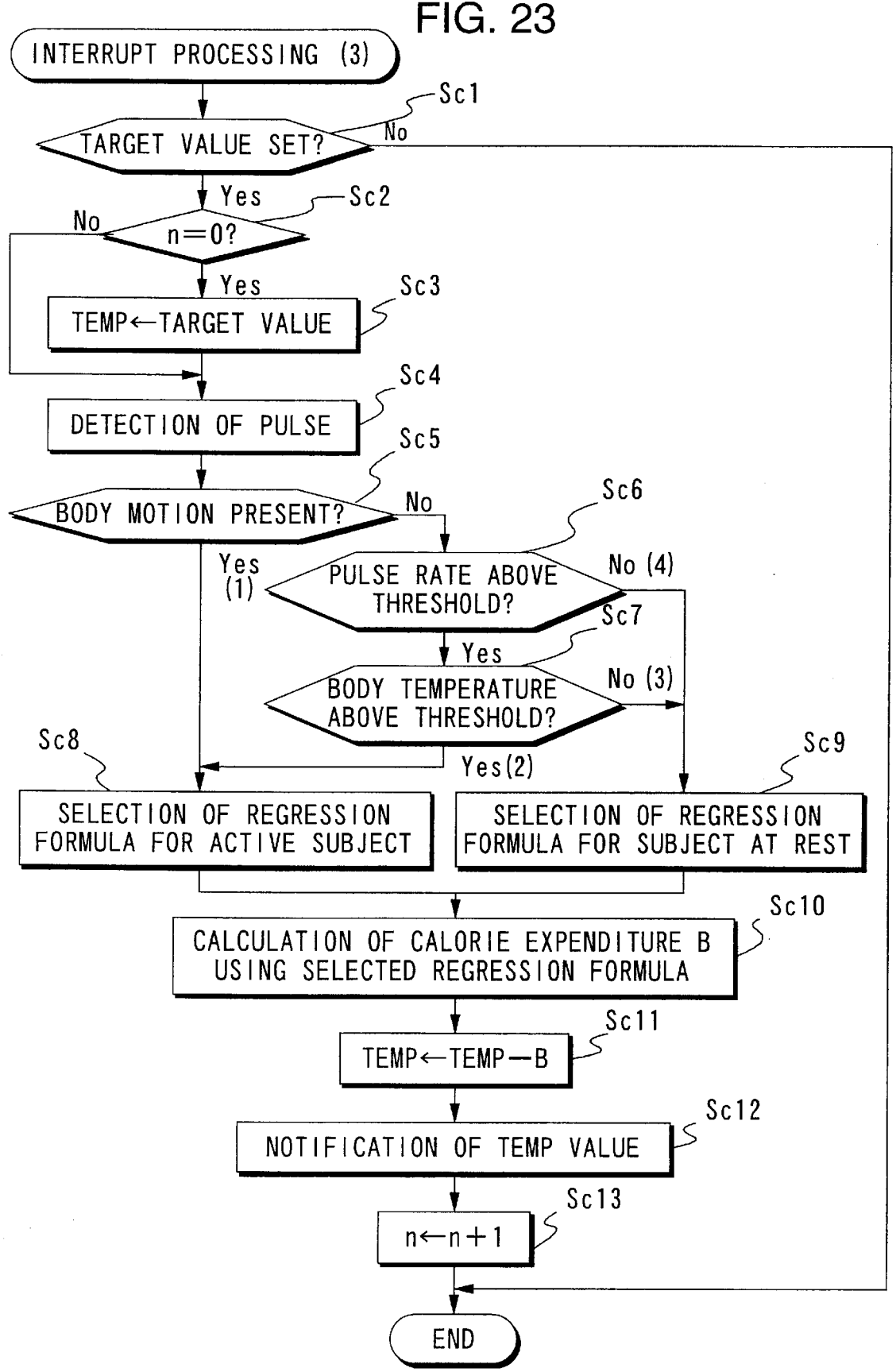

FIG. 23 is a flow chart showing interrupt processing (3) which is carried out in this device.

Figure 24:
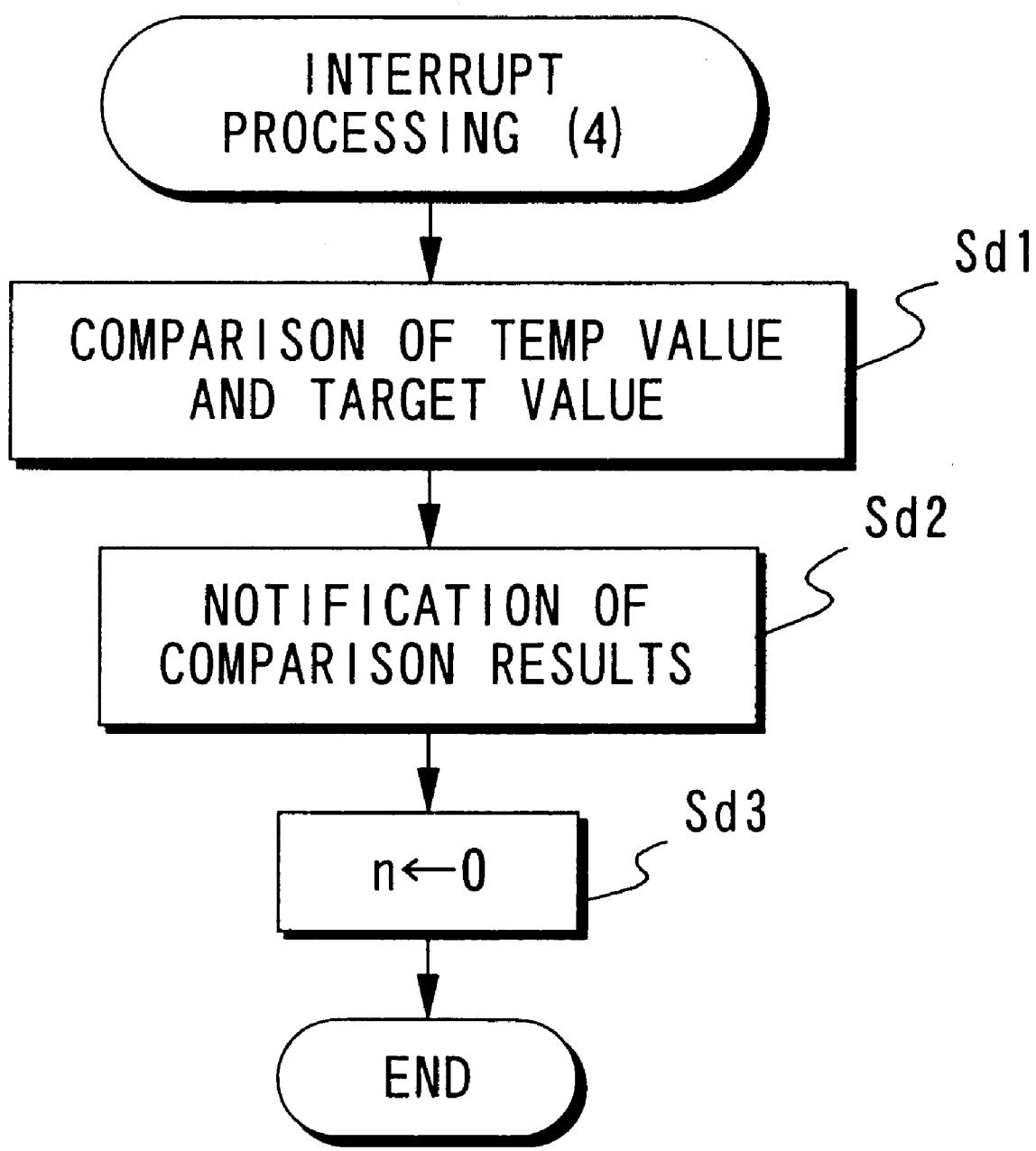

FIG. 24 is a flow chart showing interrupt processing (4) which is carried out in this device.

Figure 25A:
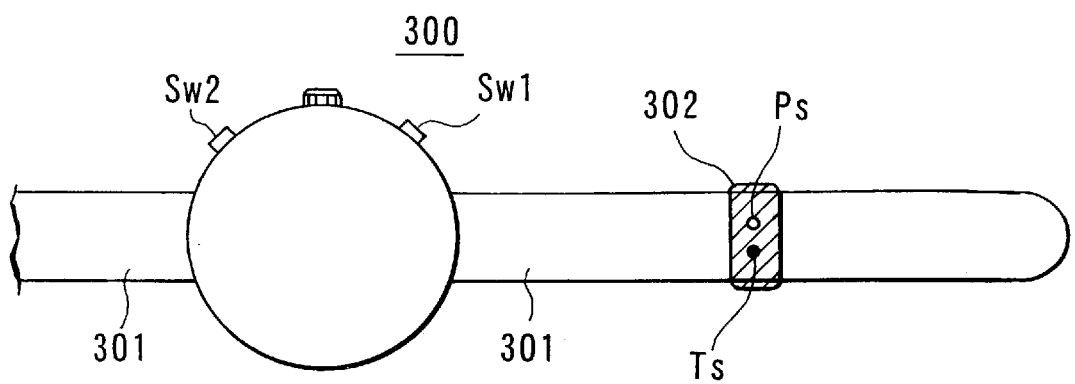
Figure 25B:
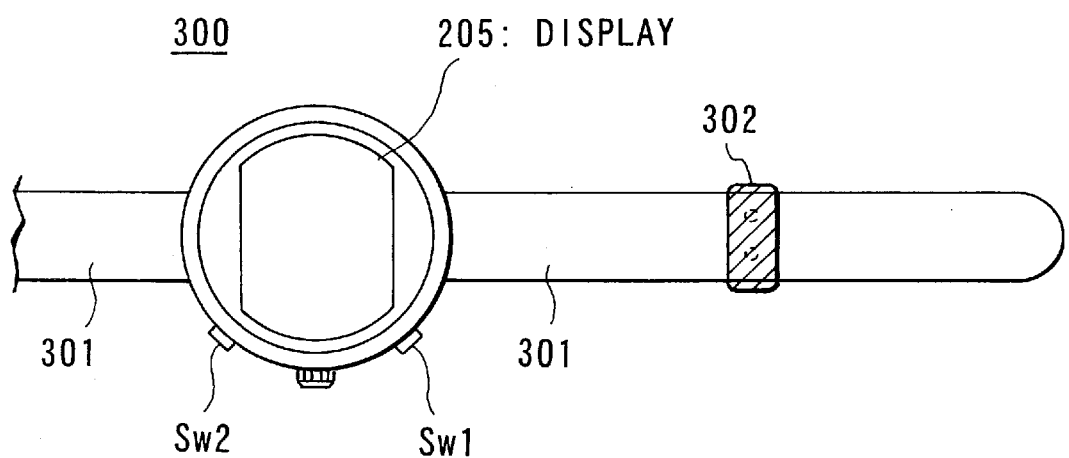

FIG. 25A is a bottom view of the external structure of the device according to another embodiment;

FIG. 25B is a planar view thereof.

Figure 26:
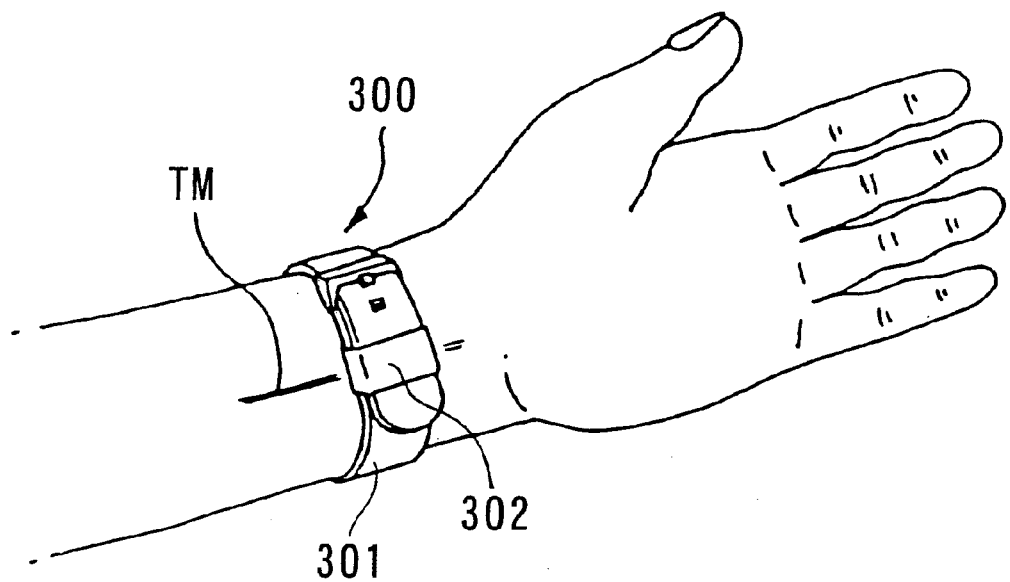

FIG. 26 is a diagram showing the state of attachment of the device in another embodiment.

Figure 27A:
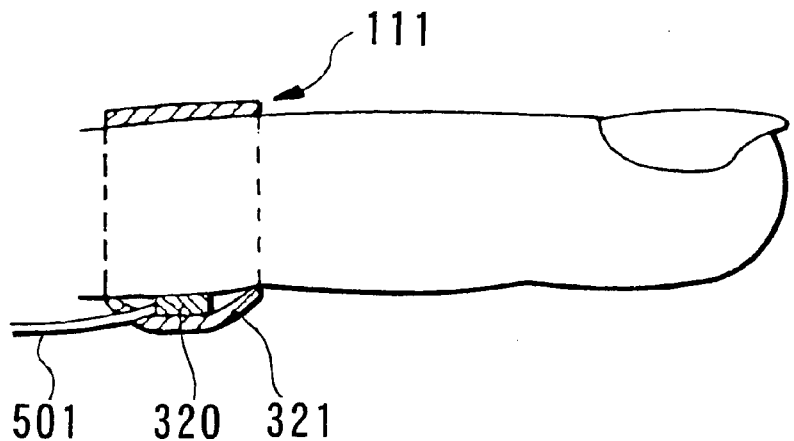
Figure 27B:
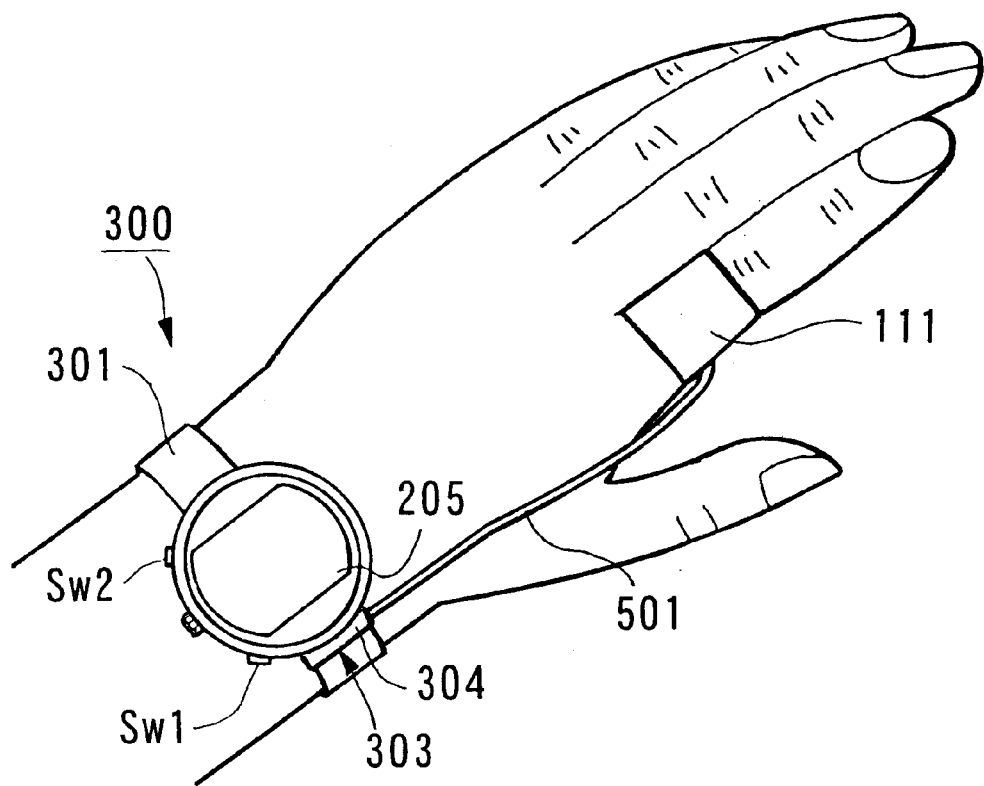

FIG. 27A is a side view of the structure of the pulse wave detector according to another embodiment;

FIG. 27B shows the state of attachment thereof.

Figure 28:
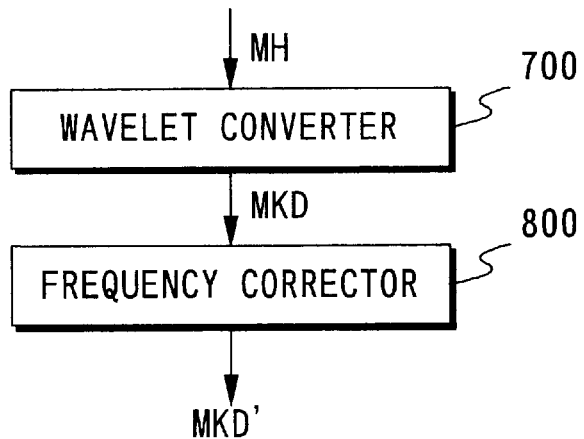

FIG. 28 is a block diagram showing the structure for carrying out wavelet conversion of the pulse wave signal.

Figure 29:
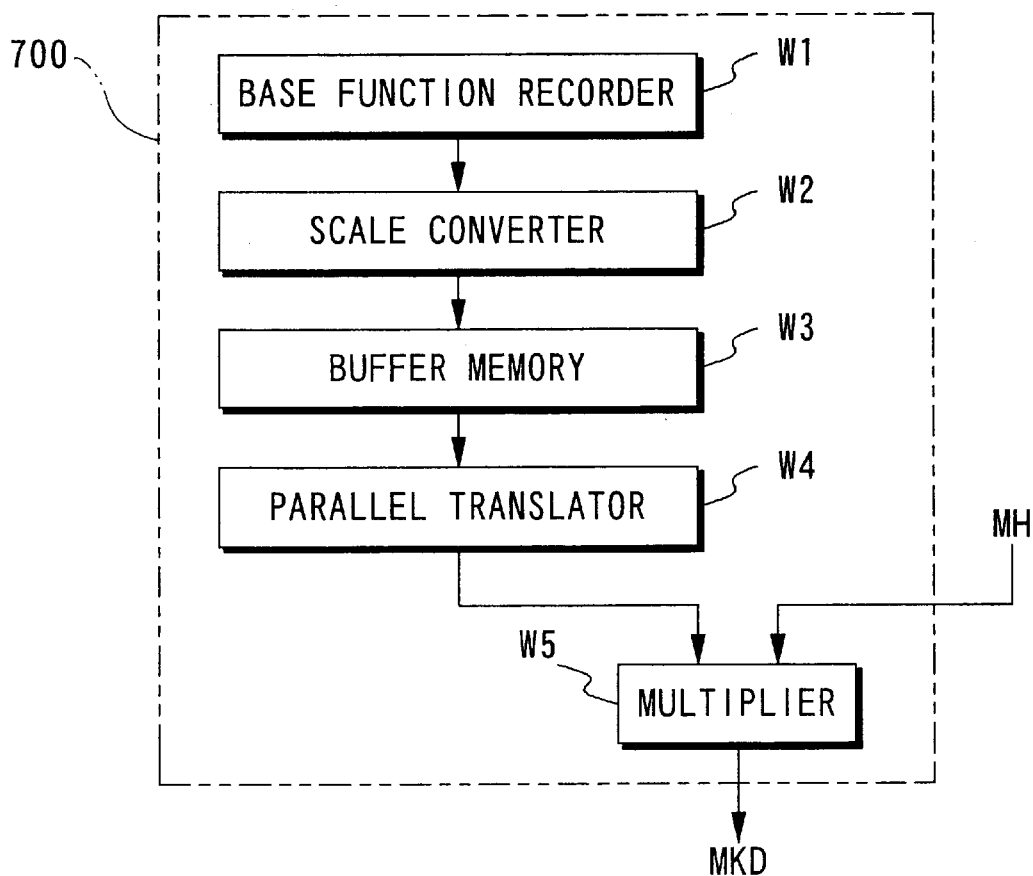

FIG. 29 is a block diagram showing the structure of the wavelet converter.

FIG. 30A is a diagram showing a one-beat component of a typical pulse waveform;

FIG. 30B is a table showing the corrected pulse wave data thereof;

FIG. 30C is an example showing specific numerical values.

Figure 31:
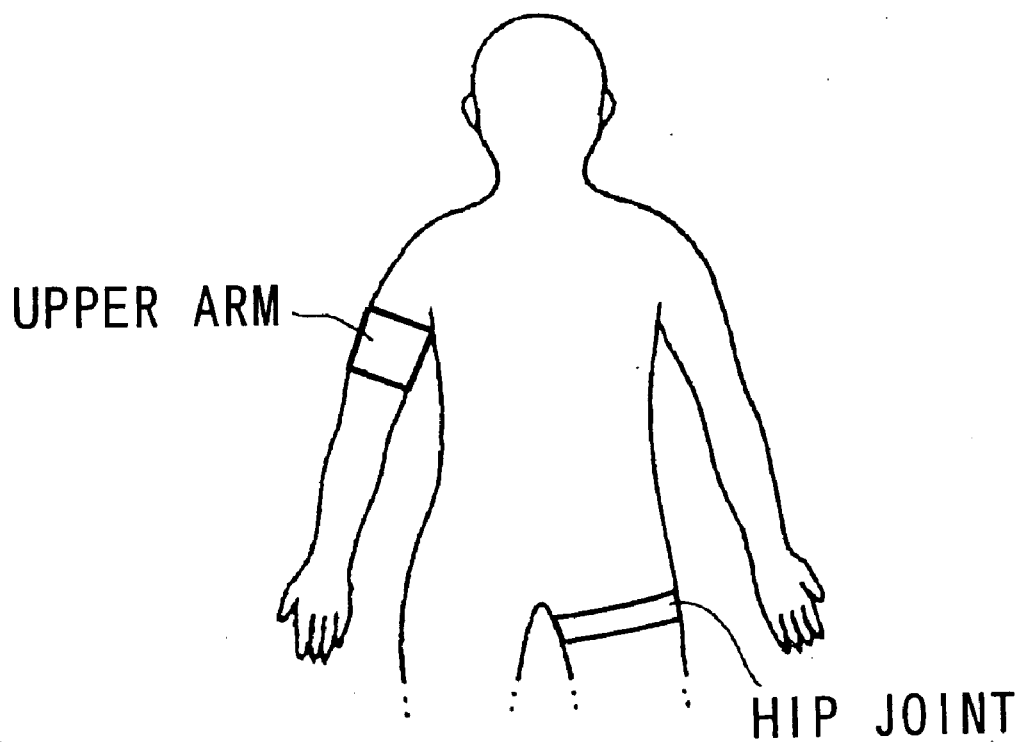

FIG. 31 is a diagram. provided to explain each of the positions on the upper arm and hip joint at which the pressure sensor and temperature sensor can be attached.

FIG. 32 is a diagram showing the external structure of the device when rendered into a necklace.

FIG. 33 is a diagram which explains the arrangement in which the pressure sensor and temperature sensor are attached to the carotid artery.

Figure 34:
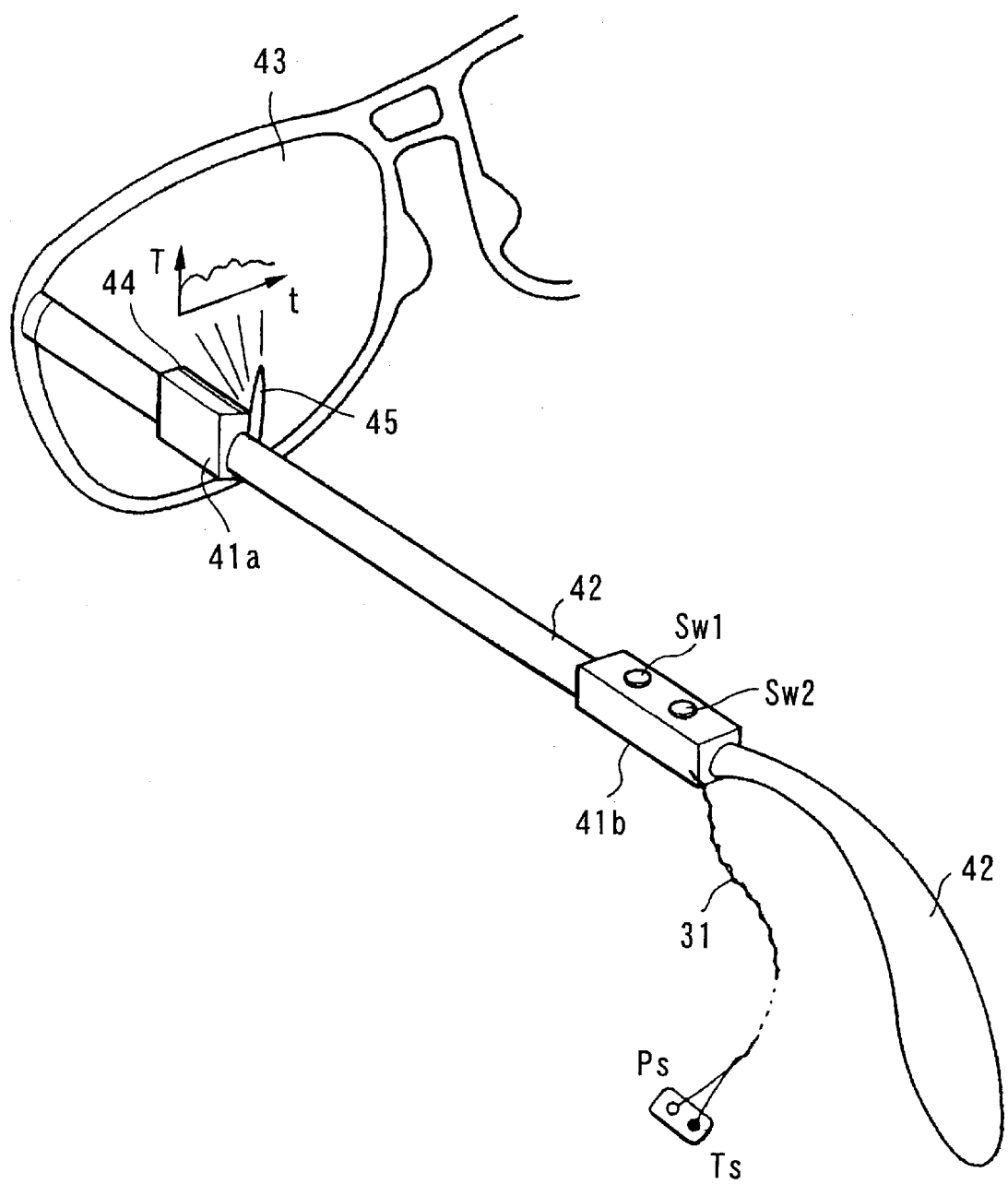

FIG. 34 shows the external appearance when the device is rendered as a pair of eyeglasses.

Figure 35:
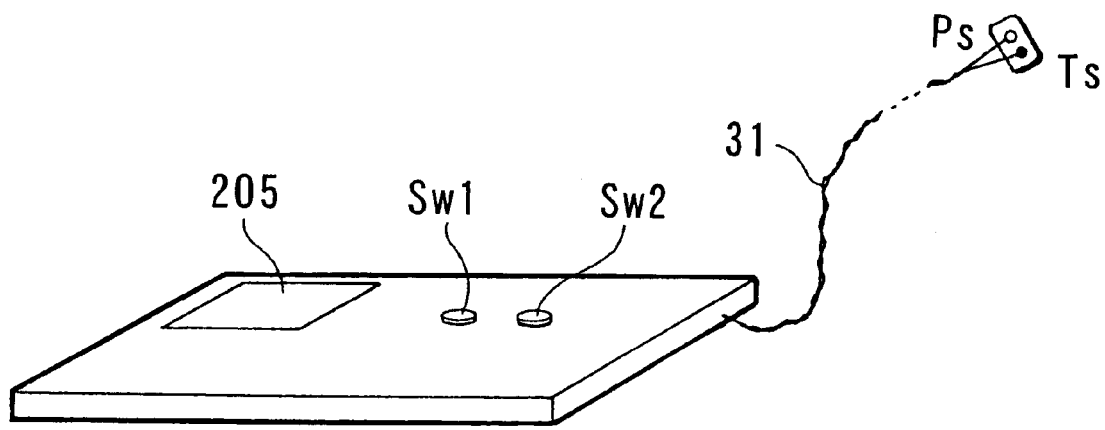

FIG. 35 shows the external appearance when the device is rendered as a pocket card.

Figure 36A:
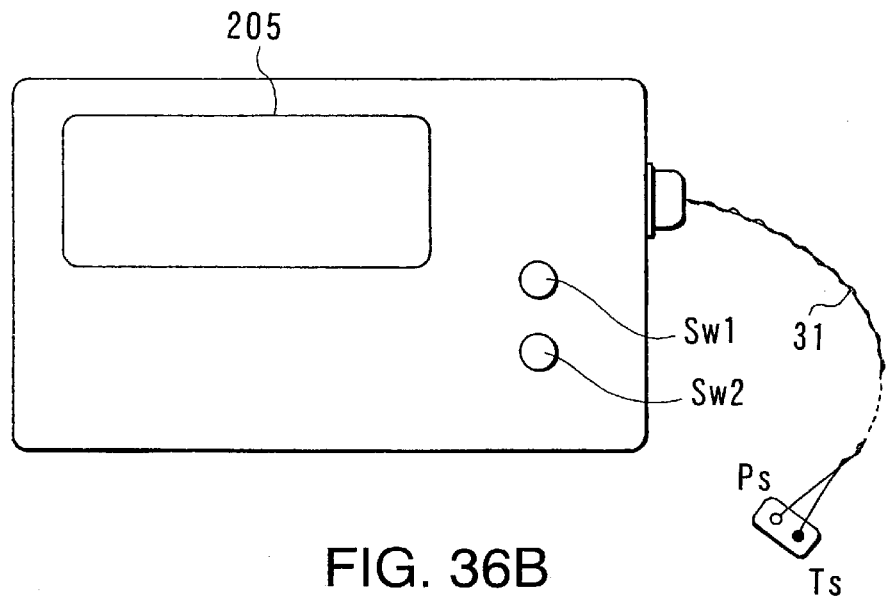
Figure 36B:
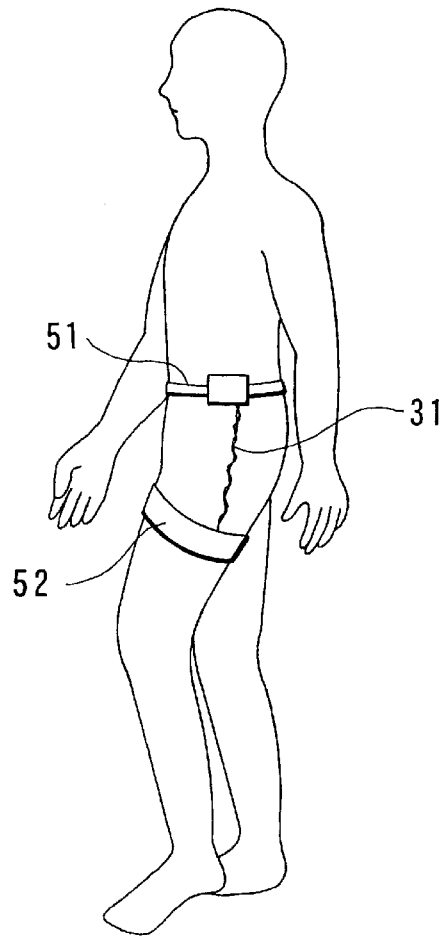

FIG. 36A shows the external appearance when the device is rendered as a pedometer;

FIG. 36B shows the state of attachment thereof.

Figure 37:
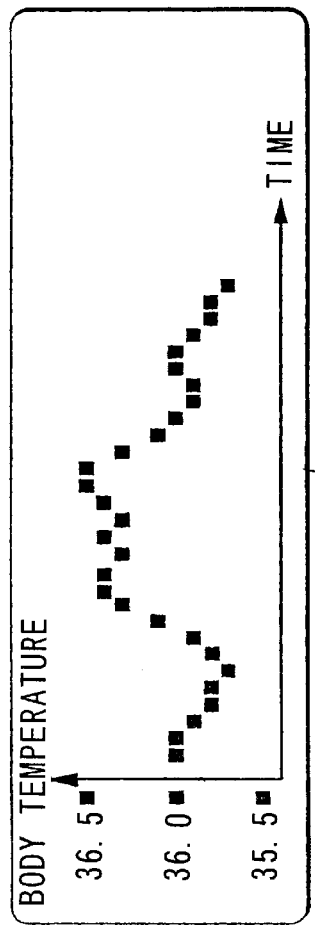

FIG. 37 shows an example of the display of the device when showing the change over time in the subject's deep body temperature.

Figure 38:
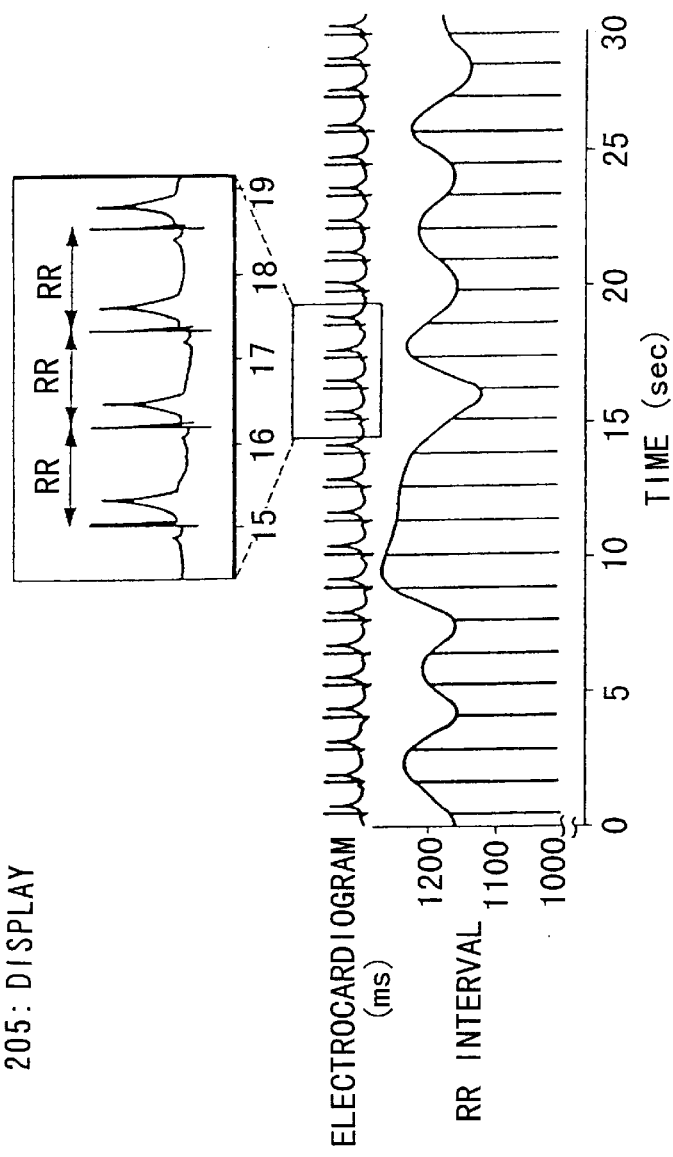

FIG. 38 shows the relationship between the heartbeat waveform in an electrocardiogram and the RR interval obtained from this waveform.

Figure 39A:
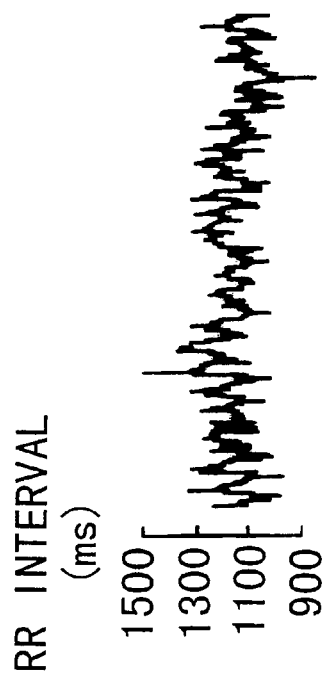
Figure 39B:
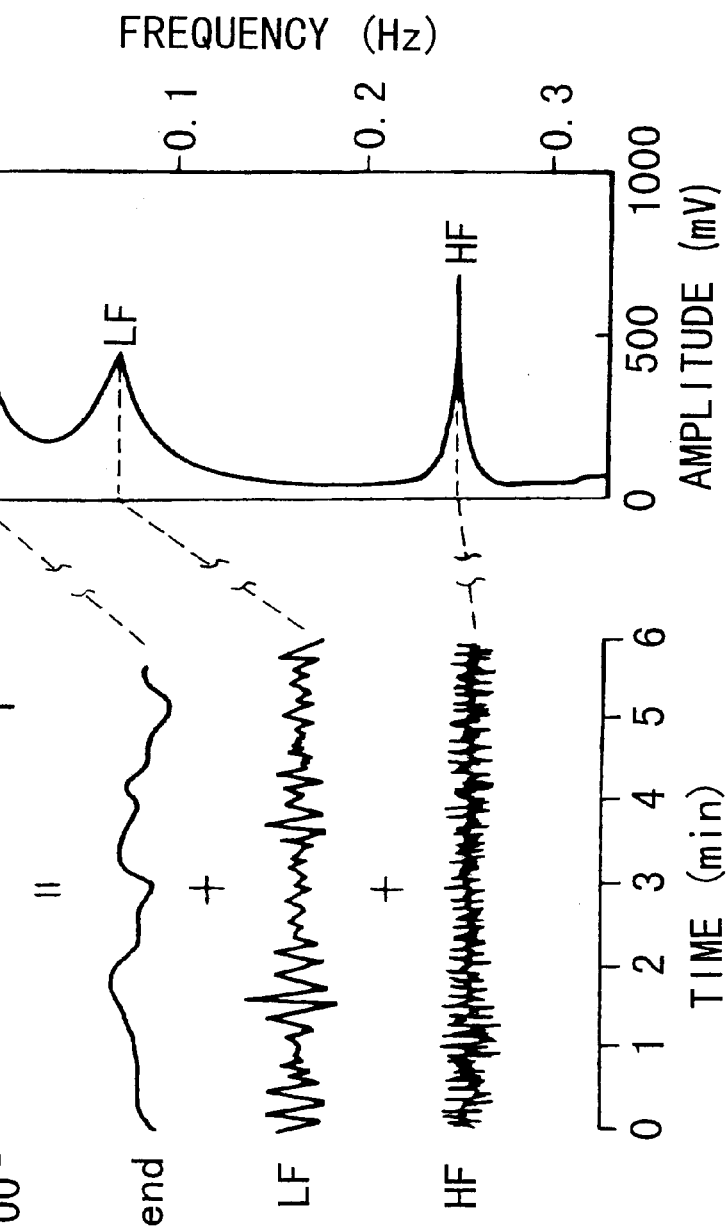

FIG. 39A shows the waves which make up the changes in blood pressure;

FIG. 39B shows the results of spectral analysis of blood pressure variation.

Figure 40:
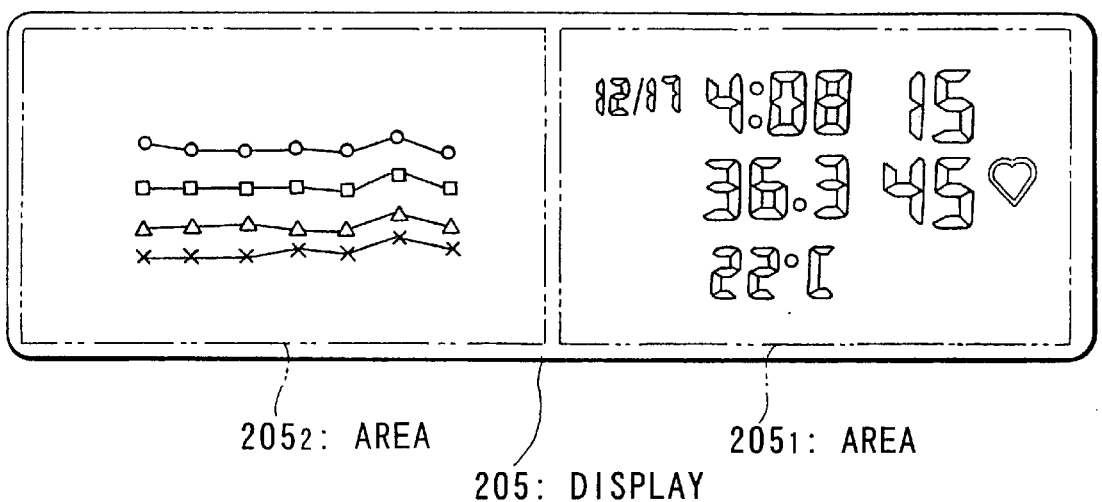

FIG. 40 shows an example of the display in this device.

Figure 41:
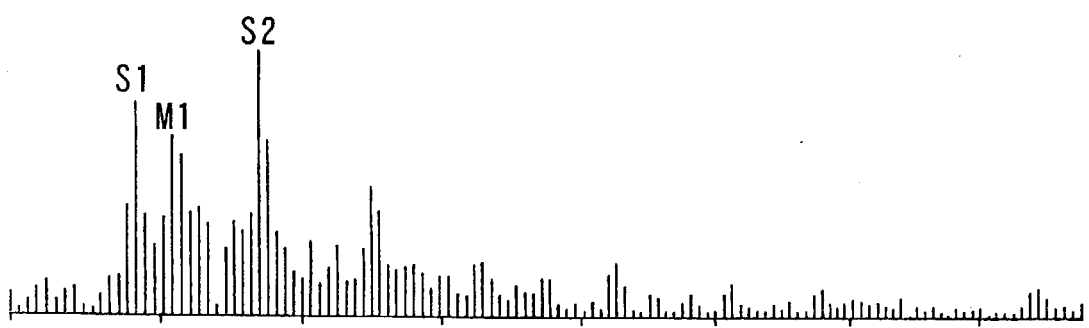

FIG. 41 shows the results of spectral analysis of the pulse waveform.

Figure 42:
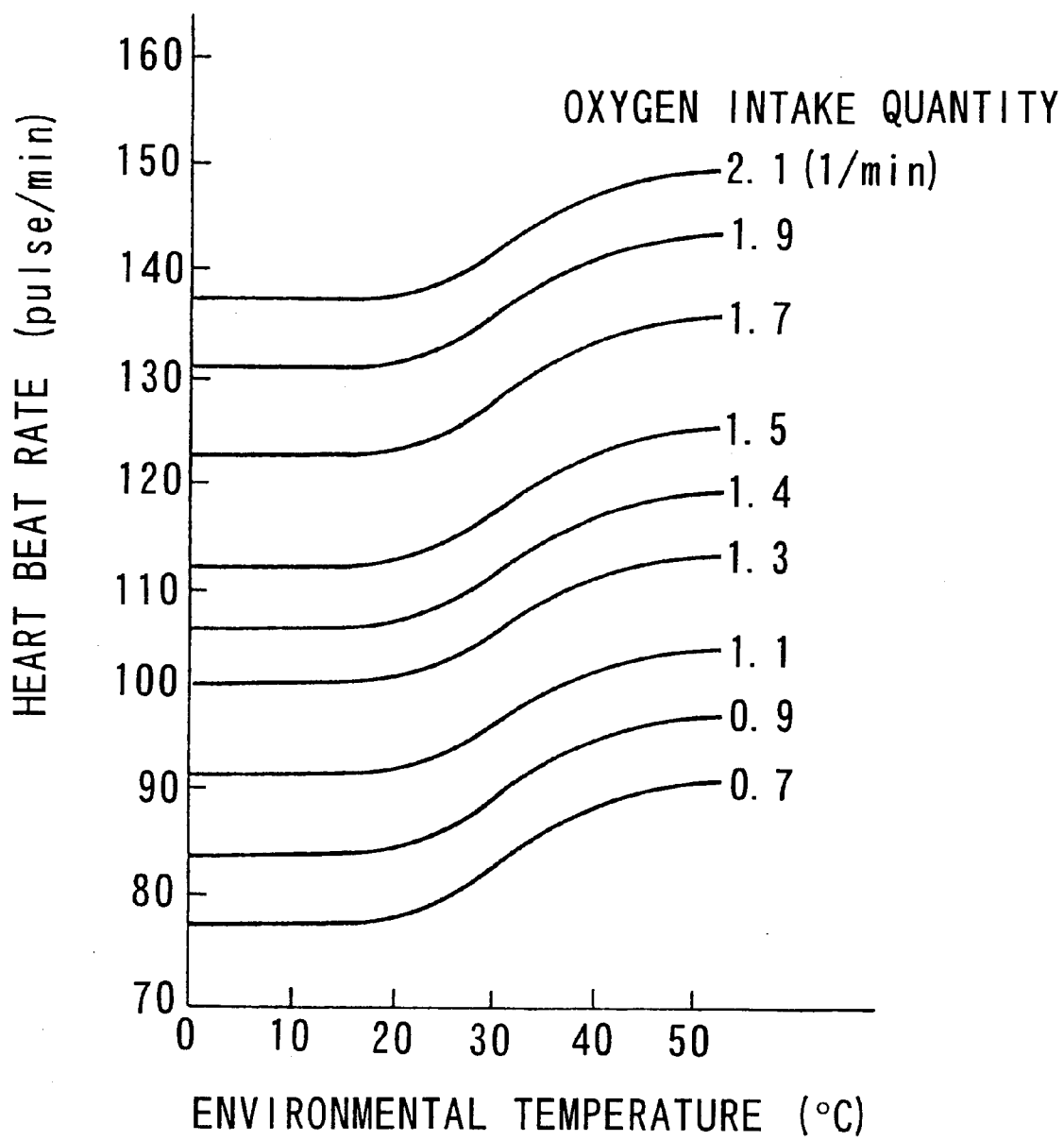

FIG. 42 shows the change in the heart rate with respect to the change in the environmental temperature.

BEST MODE FOR CARRYING OUT THE INVENTION

Preferred embodiments of the present invention will now be explained.

1: Theoretical Basis for Calculation of Calorie Expenditure

The theoretical basis for the first embodiment will now be explained. In general, there is a curved line relationship between pulse rate and the oxygen intake quantity, such as shown by the solid line in FIG. 10A.

With respect to the relationship between the quantity of oxygen consumed and the calorie expenditure, even if a coefficient of 4.85 kcal per liter of oxygen is consistently used, such as disclosed on page 206 in "Calculation of daily energy expenditure by diary profile of heart-rate" in the Employees' Pension Plan Hospital Annual Report No. 17, 1990, this does not lead to a large error. For this reason, provided that the pulse rate per unit time (beats/min) is known, then the quantity of oxygen consumed may be understood by referring to the correlations shown in this figure. If this is multiplied by the aforementioned coefficient values, then the calorie expenditure per unit time can be calculated. In other words, the correlation shown in the figure actually shows the relationship between pulse rate and calorie expenditure.

Next, the correlation shown in FIG. 10A is determined by measurement for each subject in advance. A design may be provided in which the thus obtained correlations are stored in table form, for example. In view of the fact that the change in the amount of oxygen consumed in the region where the pulse rate is low is small, while the change in the amount of oxygen consumed in the region where the pulse rate is high is large, however, a design is also acceptable in which the aboved-described relationship is divided into "aresting" and "active", and the respective relationships are expressed using linear regression formulas.

The method disclosed in Hirosaki Medicine Journal 40(1): 60–69, 1988, "Study on estimating energy expenditure by heart rate," may be used as a method for obtaining the correlation for a subject. Namely, the oxygen intake quantity during basal metabolism, such as when sleeping, may be measured using an ordinary method employing a Douglas bag, and may be measured when the subject is at rest or exercising using a commercially available respiration analyzer or the like. Further, when carrying out measurements after applying an exercise load on the subject, it is acceptable to wait for the subject's pulse rate and oxygen intake quantity to become constant, and then to gradually increase the exercise load using a treadmill or the like.

In this way, the correlation between calorie expenditure and the pulse rate corresponding to the subject is obtained in advance. Specifically, when using "resting" and "active" linear regression formulas, the information (slope, y-intercept of the regression line, etc.) for each regression formula is determined in advance.

Additionally, the regression formulas for the correlation present in the curved line relationship can be complicated, or may require much memory even if rendered into table form. In view of these disadvantages, the present embodiment incorporates a design which employs a "resting" and "active" linear regression formulas. The present invention is not limited thereto, however, but may employ a correlation which is present in the curved line relationship.

However, it is known that pulse rate may rise due to a variety of factors such as stress and the like. Accordingly, if a design is employed in which a regression formula is selected which is appropriate according to the detected pulse rate, then it is not possible to determine whether the rise in pulse rate is due to a factor other than activity, such as stress, or is due to activity performed by the subject. Thus, calorie expenditure may be incorrectly calculated.

Accordingly, as a general rule, the present embodiment employs a "resting" regression formula when the subject is at rest, and employs an "active" regression formula when the subject is in a state of activity. However, if the pulse rate and body temperature are high even when the subject is in a state of rest, then it is possible that the subject has just suspended activity, or that an abnormal condition exists. For this reason, as an exception in the embodiments, the "active" regression formula is used when the subject's pulse rate and body temperature are high, even though the subject is in a state of rest.

By selecting the regression formula in response to the subject's resting or active state, and applying the pulse rate in that regression formula, it is possible to calculate calorie expenditure per unit time with excellent accuracy.

On the other hand, physiological conditions such as body temperature and pulse rate not only change over the course of one day, but are also known to change over longer periods of time (one month or one year, for example). When these changes are compared, the change over the course of one day (hereinafter, referred to as "daily change") starts from and then returns to a standard value. Change over one month or one year (hereinafter, referred to as "monthly change" or "annual change") is change in the standard value itself over the passage of days.

The annual change in rectal temperature (body temperature) will be explained here as one example of annual changes in physiological conditions. FIGS. 11A–11D are graphs showing the change over one day in rectal temperature in a plurality of subjects, for spring, summer, fall and winter, respectively. As is clear from these figures, a human being's rectal temperature (body temperature) and the standard value thereof changes over the course of one year. The same may be said of the pulse rate, with its standard value also viewed to change over the course of one year.

However, the pulse rate at the subject's basal metabolic state in FIG. 10A is the value for obtaining the correlation, i.e., is a value which is limited to a specific time period. For this reason, setting this value as the base for the correlation does not take into consideration this type of monthly and annual change, and is thus a cause of error when calculating calorie expenditure.

Therefore, in this embodiment, the basal metabolic state is specified after continuously measuring the subject's deep body temperature, the pulse rate thereof is obtained, and the correlation is corrected after matching it to monthly and annual change in the subject's condition. In other words, this embodiment provides a design in which the information for each of the linear regression formulas is corrected by matching it to monthly and annual change in the subject's condition.

By taking this cyclical change in pulse rate into consideration in this way, it is possible to calculate calorie expenditure with excellent accuracy.

2: Embodiment

Drawing on the theoretical basis explained above, the calorie expenditure measuring device according to the embodiment of the present invention will now be explained.

2-1: Functional structure

Figure 1:
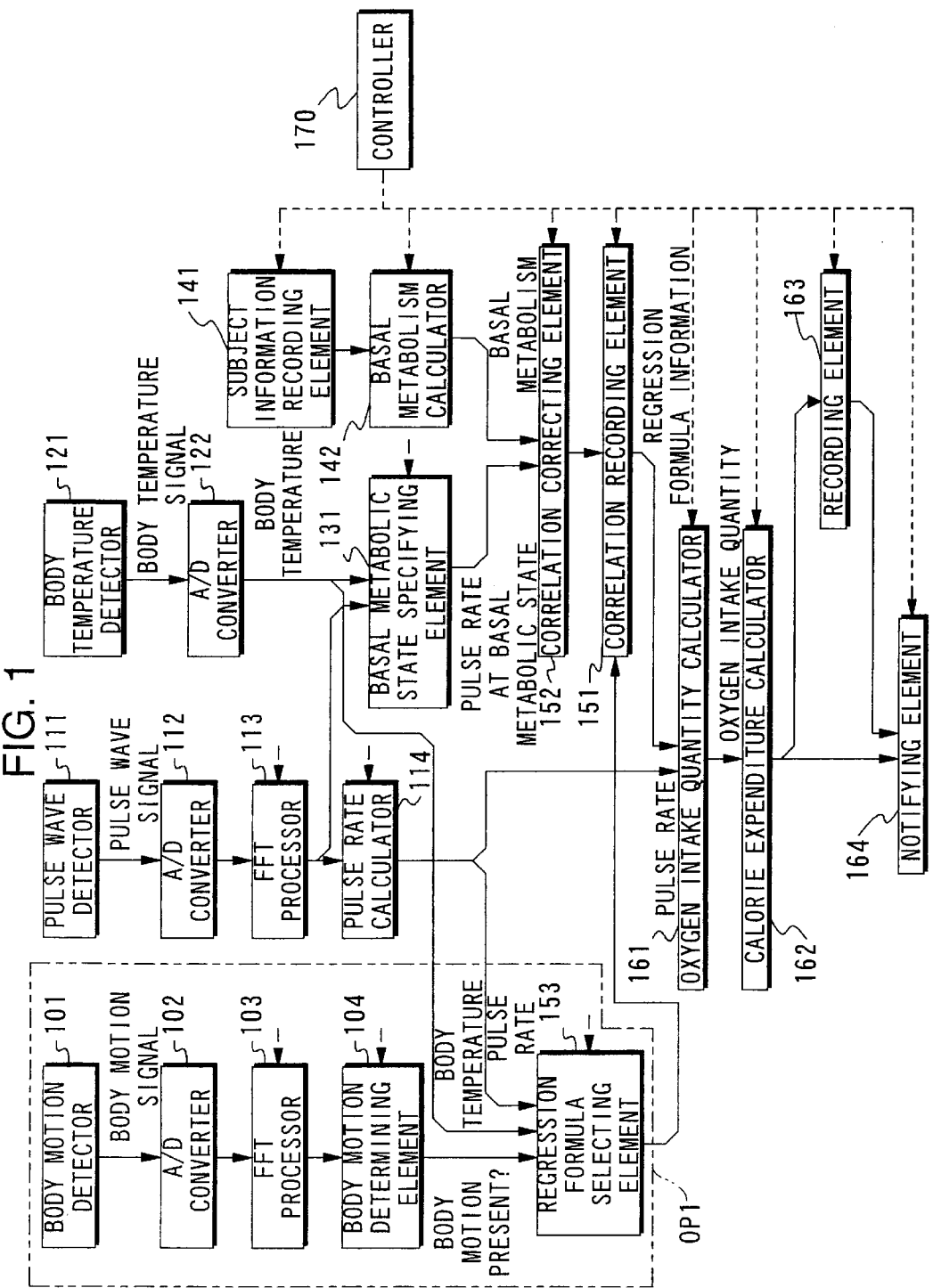
FIG. 1 is a block diagram showing the functional structure of the calorie expenditure measuring device according to an embodiment of the present invention.

The functional structure of the calorie expenditure measuring device according to the present invention will now be explained. FIG. 1 is a block diagram showing this functional structure.

In this figure, body motion detector 101 is a sensor for detecting body motion when the subject is exercising. It may be formed of an acceleration sensor, for example. The body motion signal from this body motion detector 101 is converted to a digital signal by A/D converter 102. FFT (fast Fourier transform) processor 103 uptakes over a specific interval of time the body motion signal which has been digitally converted, and executes FFT processing. Body motion determining element 104 determines whether the subject is in a state of rest or activity (exercise), based on the results of FFT processing. As a method for this determination, a method may be employed in which a determination is made as to whether or not the highest amplitude level of the frequency component has exceeded a threshold value, with the subject judged to be in a resting state when the result of this determination is negative, or to be in a state of activity when the result of this determination is positive.

Pulse wave detector 111 is a sensor which detects the subject's pulse wave. The pulse wave signal from pulse wave detector 111 is converted to a digital signal by analog to digital (A/D) converter 112. FFT processor 113 then uptakes the digitally-converted pulse wave signal over a specific period of time, and carries out FFT processing. The pulse rate is then determined from the FFT-processed pulse wave signal by pulse rate calculator 114. Note that pulse rate calculator 114 can calculate the pulse rate by determining the peak intervals of the pulse waveform taken up, and taking the inverse thereof. This will be explained below. Further, it is necessary to obtain the heartbeat rate, i.e., the number of beats of the heart per unit time, for this embodiment. However, since the heartbeat rate equals the pulse rate, a design in which pulse rate is determined is acceptable. Accordingly, it is acceptable to employ a design wherein the heartbeat is directly obtained by detecting the electrocardiogram. While a distinction is made between the pulse rate and the heart rate from a medical perspective, there is no reason to do so in the present invention. Thus, hereinafter, both heart rate and pulse rate will be referred to as "pulse rate".

Next, body temperature detector 121 measures the subject's deep body temperature (or the body temperature which is sufficiently close thereto) by means of the principles and designs described below. Body temperature detector 121 outputs an analog signal corresponding to the measured value of the temperature as the body temperature signal. The body temperature signal from body temperature detector 121 is converted to a digital signal by A/D converter 122 and output.

Deep body temperature is useful in specifying the subject's basal metabolic state. It may, however, differ from the general body temperature (obtained inside the mouth or under the arm, for example) depending on the external temperature, evaporation of sweat from the body surface or the like. The present embodiment employs a design in which a suitable regression formula is selected after taking into consideration movement and body temperature, as well as the pulse rate when calculating calorie expenditure. In this case, however, the body temperature employed is the general body temperature. Accordingly, when using the deep body temperature detected by body temperature detector 121 as the general body temperature, some sort of correction must be carried out. For the purpose of this correction, the relationship between deep body temperature and general body temperature may be rendered into table form in advance, and stored in RAM 203, for example, with the detected deep body temperature used after converting it to a general body temperature.

Next, basal metabolic state specifying element 131 specifies the subject's basal metabolic state from the FFT-processed pulse wave signal using a method which will be explained below, and outputs the pulse rate for this state.

Subject information recording element 141 records the subject's weight, height, sex and age which are set using switches Sw1, Sw2 and an external device which will be explained below.

Basal metabolism calculator 142 stores the table shown in FIG. 12 (*basal metabolism standard values per unit body surface area, Ministry of Health announcement*, 1969), and determines the subject's basal metabolism by carrying out the following calculations.

Namely, first, basal metabolism calculating element 142 determines the body surface area A [m²] from body weight W [kg] and body height H [cm] stored in subject information recording element 141 using the following formula.

Body surface area BSA=body weight $W^{0.425}$×body height $H^{0.72}$×7.184×10⁻³

For example, the average Japanese male, age 24, has a height of 1.65 [m²], while the average Japanese female, age 24, has a height of 1.44 [m²].

Second, basal metabolism calculator 142 determines the basal metabolism standard values corresponding to the age and sex of the subject which are stored in subject information recording element 141 by referencing the aforementioned table. For example, in the case of a 24-year old Japanese woman, the basal metabolism standard value is determined to be 34.3 [kcal/m² /hour].

Third, basal metabolism calculator 142 calculates the subject's basal metabolism according to the following formula.

Basal metabolism [kcal/hour]=body surface area BSA×basal metabolism standard value The explanation will now return to FIG. 1. Correlation recording element 151 stores the correlation between the calorie expenditure and the pulse rate obtained for the subject, and outputs this information. In this embodiment, correlation recording element 151 stores the information for both the regression formulas for each of the resting and active states (see FIG. 10A), and outputs the information for the regression formula selected by regression formula selecting element 153. The correlation stored in correlation recording element 151 is input via switches Sw1, Sw2, an external device, or the like, which will be explained below.

Correlation correcting element 152 corrects the correlation stored in correlation recording element 151 from the pulse rate at the subject's basal metabolic state specified by basal metabolic state specifying element 131 and from the subject's basal metabolism determined by basal metabolism calculator 142.

Specifically, with respect to the correlation stored in correlation recording element 151, correlation correcting element 152 carries out a parallel shift of uncorrected standard point P expressing the basal metabolic state, to standard point P' which is determined according to the pulse rate at the subject's specified basal metabolic state and the subject's basal metabolism. Second, correlation correcting element 152 rewrites the correlation stored in correlation recording element 151 to the correlation after the parallel shift. As a result, the correlation stored in correlation recording element 151 is corrected to match monthly and annual changes in the subject's condition. Thus, in this embodiment, the information for each linear regression formula is updated.

FIG. 10B shows a parallel transition in the x direction only. However, if the age, height or weight change, then the basal metabolism will naturally also change. In this case, correction is carried out by a parallel shift in the y direction as well.

Regression formula selecting element 153 first determines the high and low for body temperature by comparing the body temperature and the threshold value, for example. Second, regression formula selecting element 153 determines the high and low pulse rate by comparing the pulse rate and its threshold value. Third, regression formula selecting element 153 selects the regression formula which should be used for the combination of these high and low values and the presence or absence of body motion. Specifically, regression formula selecting element 153 selects the "active" regression formula in the case of (1) and (2) below, and selects the "resting" regression formula in the case of (3) and (4) below.

body motion present    (1)

body motion absent, pulse high, body temperature high    (2)

body motion absent, pulse high, body temperature low    (3)

body motion absent, pulse low    (4)

Note that "body temperature" as used here refers to general body temperature, as explained above.

Case (2) above, in which the "active" regression formula is used, is provided for the exceptional times when the subject's body is in an abnormal state or when the subject has just suspended activity. Case (3), when the subject's pulse rate is high, body motion is absent, and the body temperature is low, is viewed to be due to psychological factors, so that a "resting" regression formula is used. As a result, the present embodiment enables a more accurate calculation of calorie expenditure as compared to the conventional technology in which a regression formula is simply selected using only the high and low values for pulse rate.

When separating the correlation into "resting" and "active", as in this embodiment, it is necessary to select the regression formulas according to the subject's state. For this reason, a region OP1 is provided. If, however, a curved line regression formula or a table is employed, then this structure is not needed.

Next, oxygen intake quantity calculator 161 applies the pulse rate obtained from pulse rate calculator 114 to the correlation stored in correlation recording element 151, and determines the actual oxygen intake quantity. In this embodiment, the oxygen intake quantity is determined after applying the regression formula selected by regression formula selecting element 153. Calorie expenditure calculator 162 multiplies the obtained oxygen intake quantity by the coefficient 4.85 [kcal/l], and calculates calorie expenditure per unit time.

Recording element 163 sequentially stores the calculated calorie expenditure. Notifying element 164 carries out notification based on the calculated calorie expenditure and the stored contents of recording element 163.

Controller 170 controls the operation of all parts.

2-1-1: Principle for measurement of deep body temperature

The principle for measuring body temperature in this embodiment will now be explained. The present inventors carried out experiments using a radiation thermometer having an aperture diameter of around 5 mm to measure the temperature distribution around the area of the radial artery. The temperature roughly directly above the radial artery was just less than 1° C. higher than the surrounding area, so that a body temperature close to normal was measured. The details and results of the experiments performed by the present inventors will now be explained.

FIG. 13 shows an external view of the site at which measurements were made. The measurement of temperature was carried out along an imaginary line intersecting with the radial artery/ulnar artery when moving from the radial styloid process toward the heart 10 mm at a time. As shown in FIGS. 14A and 14B, measurement points were provided at 5 mm intervals along this line. The results of temperature measurements at each of these points is as shown in this figure. FIG. 14A shows the experimental results when the arm is dry, while FIG. 14B shows the experimental results when temperature measurements where carried out after the measurement site was immersed in water once. As is clear from these results, the temperatures above the radial and ulnar arteries are both higher than the surrounding area, with the values being close to deep body temperature. Moreover, the difference in the temperature above an artery and the temperature of the surrounding area is expressed even more clearly after immersion in water. Specifically, the temperature measured above the radial artery is not effected by immersion in water, but is nearly the same as when the arm is dry.

From a medical perspective, this phenomenon can be explained by the fact that the radial artery and other arteries carry blood, which is a heat source. Accordingly, the surface skin temperature directly above the artery is viewed to be sufficiently close to the deep body temperature, as compared to the temperature of the surrounding area. In addition, a pulse is observed directly above the radial artery which has a fast time response accompanying the output of blood from the heart. Accordingly, by finding the area in which the pulse is generated and measuring the temperature at that site, it is possible to obtain a body temperature which is sufficiently close to deep body temperature.

From the perspective of anatomy, any area is appropriate as a pulse detection site, provided that it is directly above an artery (such as the aorta, medium and small arteries) which is not extremely small. For example, the radial artery may be cited in the case of a site along a medium-sized artery, while the trunk of the finger is appropriate in the case of a small artery.

The "broad circulatory system" refers to the blood pathways named for their physical locations which distribute blood from the heart to all parts of the human body and which return the blood from those parts. FIG. 15 is provided to explain the arrangement of the broad circulatory system. In contrast, the micro circulatory system refers to circulatory units which include microscopic blood vessels which provide exchange between body fluids and tissues, lymphatic capillaries which accompany these, and the interstitium and actual tissue which surround these. As shown in FIG. 16, in the micro circulatory system, micro arteries branch into a network of capillary vessels at the ends of the arterial system, and then again congregate to form micro veins which connect to veins.

Thus, even when measuring body temperature at the radial artery or other peripheral area, it is possible to measure a body temperature which is close to deep body temperature with considerably good accuracy even after the site has been immersed in water, provided that the site is subject to normal conditions and not some unusual circumstance such as constantly soaking in water. For example, when considering an application which examines the change in body temperature when a person is sleeping, body temperature can be measured without any problems in accordance with the measurement principles described above.

Assuming the above-described principle to be true, the present invention measures a body temperature which is sufficiently close to the subject's deep body temperature by disposing a temperature and pressure sensor above the subject's radial artery, and taking the temperature detected at this site as the subject's body temperature.

It has been the conventional practice to measure deep body temperature by measuring the temperature rectally, or under the tongue or armpit. However, these devices are currently comprised of table-top equipment, while the measurement obtained at these sites was only for a single point in time. Further, these devices were typically large, so that it was not possible to carry them about in a portable fashion so that body temperature could be constantly measured.

In contrast, the present embodiment enables the measurement of a body temperature which is sufficiently near deep body temperature to be carried out comparatively simply. For this reason, a body temperature measured in this embodiment which is sufficiently close to the subject's deep body temperature is not only useful in the calculation of calorie expenditure, but is by itself extremely significant from the perspective of clinical medicine.

Accordingly, a design in which the subject or a third party is notified of the obtained deep body temperature itself, or the result of processing thereof, is also significant. This design will be explained below.

2-1-2: Specification of basal metabolic state

Next, the specification of the subject's basal metabolic state which is performed by basal metabolic state specifying element 131 of the present embodiment will be explained.

First, basal metabolic state specifying element 131 supposes a sedate period when specifying the subject's basal metabolic state. This sedate period is that time period during the day when the physiological state is closest to the basal metabolism. Ordinarily, this would be during deep sleep, and excludes REM sleep or prior to waking. Accordingly, in this embodiment, the deep sleep interval is first specified. The intensity of body movement (acceleration level) is clearly less in deep sleep than in REM sleep or prior to waking. Accordingly, the interval during which the acceleration level based on the body motion signal is below a threshold value can be specified as the deep sleep interval.

Moreover, ordinarily, this type of deep sleep interval is considerably longer than the sedate period which is being determined. As discussed above, physiological state changes on a daily cycle, such that the standard value can only be obtained during a small interval of time. Accordingly, when the sedate period is taken as a long period of time on the order of the deep sleep interval, then the representative value during this interval may differ greatly from the standard value. In other words, the sedate period should be determined by specifying the deep sleep interval more precisely. Thus, in this embodiment, a sedate period which is sufficiently short is obtained by monitoring changes in body temperature.

In general, body temperature is known to follow daily change, with the curve thereof shifting from descending to ascending to match basal metabolic state. Thus, in this embodiment, the curve for body temperature during the interval when measurements were made is obtained. When, from among the inflection points along the curve, an inflection point at which a minimum value is obtained is within the deep sleep interval, then a specific time interval around the inflection point is specified as the sedate period. The curve for body temperature can be obtained using a conventional method (least squares method, for example) to determine the formula for the curved line which most closely fits each point specified by the body temperature input during the specific time interval and each time of input.

Note that it is also acceptable not to consider the deep sleep interval, but to specify the specific time period around an inflection point at which a minimum value was obtained along the curve for the body temperature as the sedate period. However, since the inflection point at which a minimum value is obtained may appear outside the deep sleep interval depending on the state of use or the subject's biorhythms, this embodiment employs both the deep sleep interval and the body temperature curve. Further, when the threshold value which becomes the standard for determining the deep sleep interval is set to be sufficiently small, so that the deep sleep interval is sufficiently short, then it is possible to use the deep sleep interval as is for the sedate period.

Further, when detecting physiological information obtained during a sedate period specified in this way, the physiological information is the value which should be the standard for monthly and annual physiological change. As in the case of the deep body temperature, this physiological information is not only useful in the calculation of calorie expenditure, but is also extremely significant by itself.

Accordingly, a design which notifies the subject or a third party of the physiological information obtained during the sedate period, or the result of processing thereof, is naturally significant. This design will be described below.

2-2: Electrical structure

Figure 2:
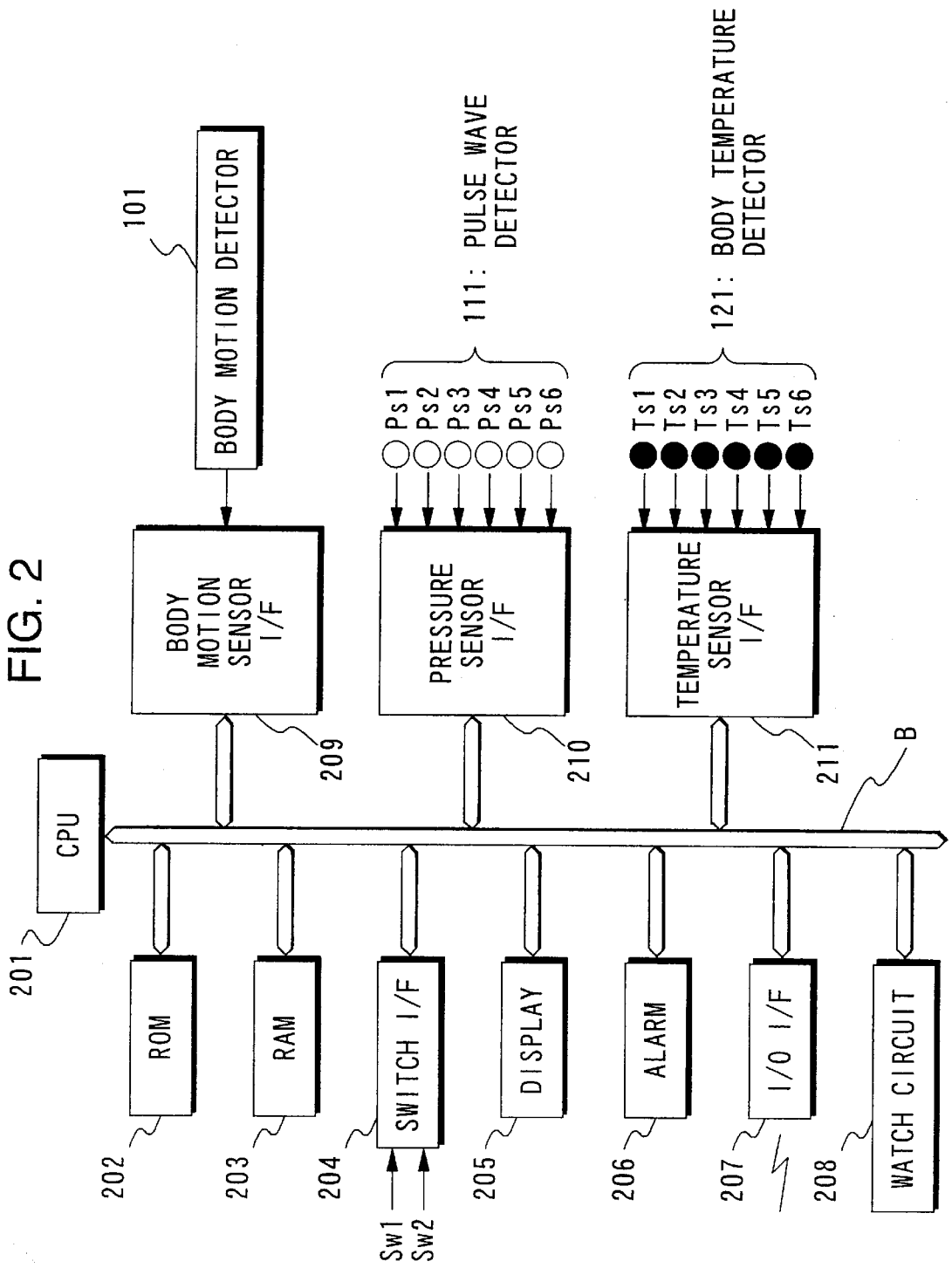
FIG. 2 is a block diagram showing the electrical structure of the same device.

Next, the electrical structure for realizing the functional structure shown in FIG. 1 will be explained. FIG. 2 is a block diagram showing this structure.

CPU 201 carries out control of various parts via bus B, as well as executing various processing and calculations based on basic programs stored in ROM 202. CPU 201 corresponds to the FFT processors 103,113, body motion determining element 104, pulse rate calculator 114, basal metabolic state specifying element 131, basal metabolism correcting element 142, correlation correcting element 152, regression formula selecting element 153, oxygen intake quantity calculator 161, calorie expenditure calculator 162, and controller 170.

RAM (random access memory) 203 stores the measured value of each of the sensors which will be explained below, and the results of the calculations. It corresponds to the operational area when CPU 201 is carrying out calculations, is employed as a storage area for target values, and corresponds to subject information recording element 141, correlation recording element 151 and recording element 163 shown in FIG. 1.

Switch interface 204 detects the operational state of switches Sw1 and Sw2, and informs CPU 201 to that effect. These switches may be provided in a portable device such as a wristwatch. Switch Sw1 is used to indicate the start or stop of measurement of calorie expenditure. Switch Sw2 is used to select the various functions (modes).

Display 205 is provided on a portable device such as a wristwatch, in the same manner as switches Sw1, Sw2. It displays various information under the control of CPU 201, and is, for example, formed of an LCD (liquid crystal display panel). Alarm 206 sounds an alarm under the control of CPU 201, in order to notify the subject of a change in the various states. Display 205 and alarm 206 correspond to notifying element 164 in FIG. 1. Further, I/O interface 207 has an LED and a phototransistor, and is for sending and receiving information with an external device.

Watch circuit 208 has the functions of an ordinary wristwatch, as well as the functions for carrying out various interrupt processing by sending an interrupt signal to CPU 201 at time intervals determined in advance. For this reason, CPU 201 can read out the current time from watch circuit 208.

Body motion sensor interface 209 samples the body motion signal from body motion detector 101 at specific intervals, and outputs the body motion signal after digitally converting it. Body motion sensor interface 209 corresponds to A/D converter 102 in FIG. 1.

Pressure sensors Ps1~Ps6 are sensors for measuring the pulse pressure around the subject's radial artery. They output the analog electrical signal which corresponds to the pulse pressure at this area as a pulse wave signal, and together correspond to pulse wave detector 111. Pressure sensor interface 210 samples the pulse wave signals from pressure sensors Ps1~Ps6 at specific time intervals, and outputs the pulse wave signal after digitally converting it. It corresponds to A/D converter 112 in FIG. 1.

Temperature sensors Ts1~Ts6 are disposed about pressure sensors Ps1~Ps6, and each measure the temperature of the skin surface around the radial artery. The analog electrical signal corresponding to the measured value of the temperature is output as the body temperature signal. Temperature sensors Ts1~Ts6 together correspond to body temperature detector 121 shown in FIG. 1. Temperature sensor interface 211 samples the body temperature signals from temperature sensors Ts1~Ts6 at specific time intervals, and outputs them after conversion to a digital signal. It corresponds to A/D converter 122 in FIG. 1. A temperature sensor which employs thermocouples is preferably used from the perspective of conversion efficiency. However, it is also acceptable to use a temperature sensor which employs temperature characteristics like reverse current, such as a thermoelement like a thermocouple, thermister, diode, transistor, or the like.

2-3: External structure

In this way, the present embodiment employs a combination of pressure sensors Ps1~Ps6 and temperature sensors Ts1~Ts6. The external appearance of the device will now be explained with reference to FIG. 3.

Figure 3A:
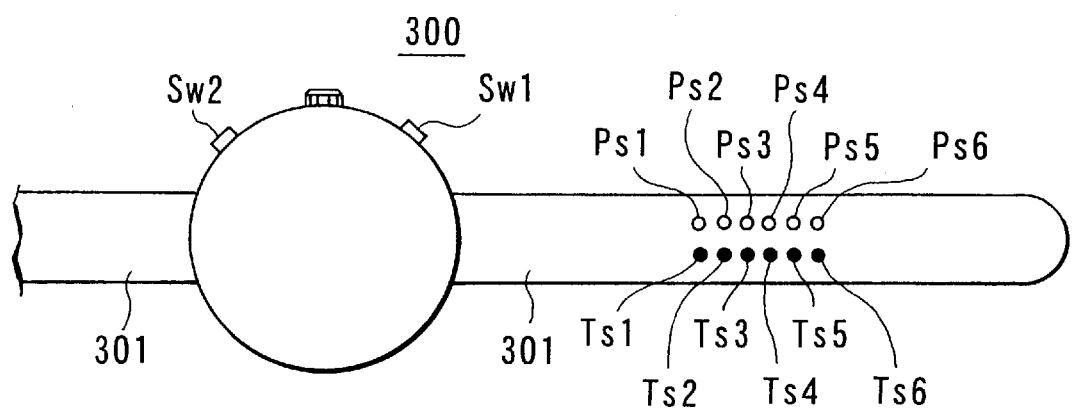
FIG. 3A is a bottom view showing the outer appearance of the same device; FIG.

FIG. 3A is a bottom view of the calorie expenditure measuring device according to this embodiment. Switches Sw1 and Sw2 have been provided to the side of device main body 300 which is designed in the form of a wristwatch. Pressure sensors Ps1~Ps6 and temperature sensors Ts1~Ts6 are aligned in a row along the longitudinal direction of band 301.

More specifically, pressure sensor Psi (i=1~6) and temperature sensors Tsi (i=1~6) are disposed about the direction of the width of band 301. These pressure sensors Psi and temperature sensors Tsi form pairs. Band 301 wraps around the wrist of the subject, so as to be in tight contact with the surface of the skin around where the radial artery runs.

Figure 3B:
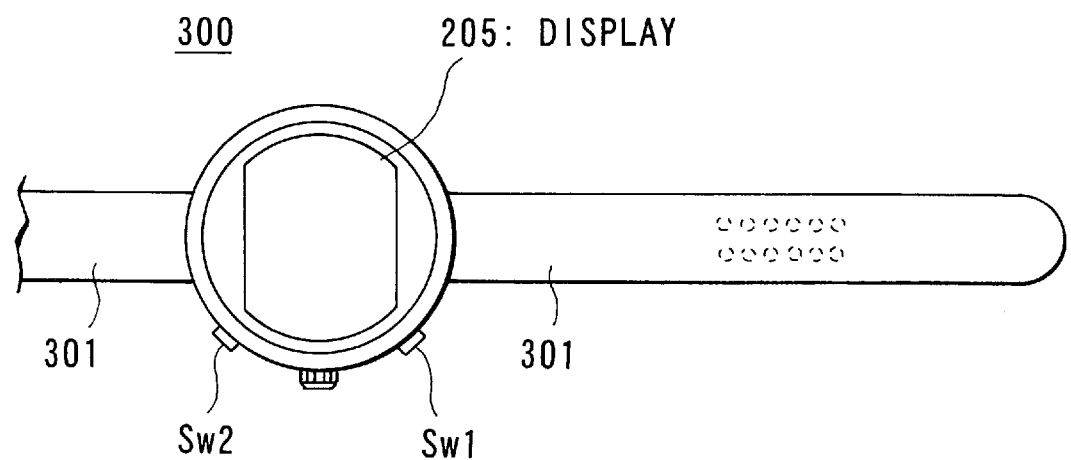

FIG. 3B is a planar view of the calorie expenditure measuring device according to this embodiment. A display 205 is provided to the upper surface thereof. An LED which serves as a transmission element and a phototransistor which serves as a receiving element are provided to device main body 300 for carrying out optical transmission with an external device to be explained below (LED and phototransistor not shown).

2-4: Detailed Structure of Temperature Sensor and Pressure Sensor

An example of the specific structure of the temperature sensor and pressure sensor will now be explained. The sensor discussed below is one developed by the present inventors and corresponds to the pressure sensor disclosed in Japanese Patent Application, Laid Open No. Hei 6-10144 (Title of the Invention: Pressure sensor, and pressure vibration detection device and pulse wave detection device employing said sensor).

FIG. 4 shows the structure of the temperature and pressure sensors according to the present invention. FIG. 4A is a partial cross-sectional perspective view of the pressure sensor in cross-section; and FIG. 4B is a transparent perspective view of the pressure sensor in cross-section. The sensor shown in these figures correspond to one pair consisting of pressure sensor Ps1 and temperature sensor Ts1 shown in FIGS. 2 and 3, for example.

In FIG. 4A and 4B, pressure sensor 60 is formed from pressure sensitive elements S1~S4 and semispherical elastic rubber 61. The shape of elastic rubber 61 is taken to be a perfect semisphere hereinafter. Pressure sensitive elements S1~S4 are disposed to the lower surface L of elastic rubber 61, and respectively output as detected signals voltages V1~V4 which are proportional to the detected pressures. The (x, y) coordinates of detection positions Q1~Q4 of these pressure sensitive elements S1~S4 are (a,0), (0,a), (−a,0), and (0,−a) respectively, when the radius of elastic rubber 61 is r, the center of the lower surface L is the origin (0,0), and r>a>0. Namely, the coordinates at which pressure is to be detected by pressure sensitive elements S1~S4 are on the x and y axes on the lower surface L and are separated from the origin by an equal distance a.

Temperature sensor 62 is formed of a thermocouple, and is disposed at the center (i.e., origin) of lower surface L. Lead wires 80,80 which are connected to the leads of the thermocouple are connected to temperature sensor interface 211 of FIG. 2. As shown in FIG. 4A or 4B, when temperature sensor 62 is disposed in the same plane as pressure sensitive elements S1~S4, then an accurate temperature measurement in the tissues above the arteries can be realized when measuring the body temperature. Further, the area occupied by temperature sensor 62 on lower surface L is preferably designed to be less than the surface area occupied by each of the pressure sensitive elements S1~S4 on lower surface L. Thus, if the area occupied by temperature sensor 62 is small, the thermoelectric exchange efficiency improves by that amount.

Next, with reference to FIG. 5, joining between each of the pressure sensitive elements and elastic rubber 61 will be explained using pressure sensitive element S1 as an example. As shown in this figure, semiconductor substrate 63 is adhered to lower surface L of elastic rubber 61 by means of adhesive layer 64 which has an elastic quality. In addition, pressure sensitive element S1 which detects pressure at detection position Q1 is formed in semiconductor substrate 63 together with hollow chamber $65_{-1}$ which opens on the detection position. Pressure sensitive element S1 is formed from thin element $66_{-1}$ which is 20 to 30 μm in thickness and which is employed as a diaphragm, and from distortion gauge $67_{-1}$ which is formed to the surface of thin element $66_{-1}$.

Pressure-sensitive element S1 is formed using a known technique for etching semiconductors. In particular, distortion gauge $67_{-1}$ is formed of a piezo resistance element (p-type resistance layer) which is formed using a selective dispersion technique for impurities (i.e., boron, etc.). When this type of distortion gauge $67_{-1}$ bends, the resistance value varies in response to the distortion.

Similarly, pressure-sensitive elements S2~S4 are formed on top of semiconductor substrate 63, with the resistance values thereof varying respectively in proportion to the pressure at detection positions Q2~Q4.

When a pressure vibration is generated on the semispherical surface of elastic rubber 61 in a pressure sensor 60 of the above described structure, it is propagated as an elastic wave through elastic rubber 61, and becomes microvibrations at detection position Q1. causing a change in the pressures inside hollow chambers $65_{-1}$. In this case, distortion gauge $67_{-1}$ bends under the difference between the pressure inside hollow chamber $65_{-1}$ and the outside pressure introduced by opening $68_{-1}$ which is open to the outside environment. As a result, the resistance value changes in response to the pressure vibration. Aluminum electrodes (not shown) for directing the external circuits are deposited to each end of distortion gauges $67_{-1}$–$67_{-4}$. The electrodes can be respectively converted between resistance and voltage by means of the circuit described below, with the voltage output as a detected voltage V1~V4 proportional to the pressures at detection positions Q1~Q4.

Next, the electrical connection between pressure sensitive elements S1~S4 and the bias thereof will be explained with reference to FIG. 6. In this figure, distortion gauges $67_{-1}$ to $67_{-4}$ are all shown as equivalently variable resistors. As shown in this figure, each of distortion gauges $67_{-1}$ to $67_{-4}$ corresponding to pressure sensitive elements S1~S4 are connected in series, with output terminal 69, . . . , 69 provided to the respective ends thereof. Both ends of the distortion gauges $67_{-1}$ to $67_{-4}$ series are connected to bias circuit 70.

This bias circuit 70 is formed of constant-current circuit 71, switch 72 which turns on and off the output signal from constant-current circuit 71, and switching circuit 73 which turns switch 72 on when control signal T is at a high level. The device is designed so that when control signal T is at a high level, the output signal from constant current circuit 71 is impressed on distortion gauges $67_{-1}$ to $67_{-4}$. The resistance value of the distortion gauge changes in response to bending as described above, so that when the same fixed current flows though each of distortion gauges $67_{-1}$ to $67_{-4}$, the voltages V1~V4 between output terminals 69, . . . 69, are proportional to the pressures at detection positions Q1~Q4, and relatively indicates the size of that pressure.

An embodiment such as shown in FIG. 7 may also be considered as another example for realizing the provision of a temperature sensor in elastic rubber 61. This embodiment employs a thermocouple array for temperature sensor 62. A circular opening 81 is provided in elastic rubber 61, while a cylindrical waveguide 82 is punched through elastic rubber 61 having as a center axis the lead wire which passes through temperature sensor 62. As a result, temperature sensor 62 receives the energy radiated from the body which is opposite elastic rubber 61, and measures the temperature. The diameter of cylindrical waveguide 82 is roughly twice that of temperature sensor 62. As one variation of the embodiment shown in FIG. 7, a design may also be considered in which an optical means which collects light, such as a lens system, is provided along waveguide 82.

Next, the principle for measuring the pulse wave using pressure sensor 60 will be explained. Note that the arteries which are discussed below all pass through the skin surface. As shown in FIG. 8, the semispherical side of elastic rubber 61 is pressed in the vicinity of artery 75. A vibration occurs at point Pn on the semispherical surface of elastic rubber 61 due to a pressure vibration wave (i.e., pulse wave) generated from artery 75. In this discussion, point Pn is assumed to be the vibrational center. The vibration is propagated through elastic rubber 61, detected by pressure-sensitive elements S1~S4 as a detection signal having electrical signals (i.e., voltages V1~V4) indicating pulse waves, and output. Note that in FIG. 8, numeral 76 indicates subcutaneous tissue of the arm.

The pressure sensor interface 210 shown in FIG. 2 samples the voltages V1~V4 detected by pressure sensitive elements S1~S4, carries out A/D (analog/digital) conversion, and relays the converted voltages to bus B. In this explanation, the four voltages V1~V4 undergo A/D conversion, however, it is also acceptable to convert any number of voltages. CPU 201 selects the largest of these voltages, and carries out A/D conversion on one of these.

2-5: External device

Next, the external device which carries out sending and receiving of information with the device of the present invention will now be explained with reference to FIG. 9. As shown in this figure, the external device is formed of a device main body 600, display 601, key board 602, printer 603 and the like. It is equivalent to an ordinary personal computer, with the exception of the following points.

Namely, device main body 600 internally houses an optical interface consisting of a transmission controller and a receiving controller, which are not shown in the figures, for sending and receiving data by means of optical signals. The transmission controller is provided with LED 604 for sending optical signals, and the receiving controller is provided with a phototransistor 605 for receiving optical signals. The devices employed for LED 604 and phototransistor 605 have characteristics which are the same or very similar to the characteristics of the LED and phototransistor provided to device main body 300 of the calorie expenditure measuring device. A device employing near infrared (having a central wavelength of 940 nm) is preferable, for example. When employing a device which uses near infrared, a visible light cutting filter for blocking visible light is provided to the front surface of device main body 600, forming a transmission window 606 for transmitting optical communications.

Information is sent and received between an external device such as described above and the device main body 300 of the calorie expenditure measuring device by means of optical communications. The details of the sending and receiving of information will be explained together with the operation of the device.

While the present embodiment carried out the communications functions by means of optical communications, a variety of other arrangements may be considered such as wireless communications using electric waves or wired communications via cables.

2-6: Operation

The operation of the calorie expenditure measuring device according to the present embodiment will now be explained.

Device main body 300 has the structure of a wristwatch, and therefore has the functions of a wristwatch in addition to functions for measuring calorie expenditure. However, since the wristwatch functions do not directly relate to the present invention, the following explanation will focus mainly on functions associated with the measurement of calorie expenditure.

First, the subject tries to wear device main body 300 whenever possible, provided it is not inconvenient, and depresses switch Sw1 when it is necessary to know the calorie expenditure. CPU 201 recognizes the depression of the switch via switch interface 204, sequentially reads out pulse wave signals from pressure sensors Ps1~Ps6 via pressure sensor interface 210, and stores these in RAM 203.

Once the intake processing is completed, CPU 201 selects the maximum value from among the six measured values for pressure, and specifies the pressure sensor at which the maximum pulse pressure was measured. Thereafter, this specified pressure sensor, and its matching temperature sensor are employed for measurements.

2-6-1: Specification of basal metabolic state

Next, the operation to specify the basal metabolic state in this embodiment will be explained. Note that the following processing presupposes that the subject's body weight, height, sex, age and correlations (information of each linear regression formula) have been preset in RAM 201 (i.e., subject information recording element 141 and correlation recording element 151) using Sw1, Sw2 (or the external device). This correction is carried out daily during the measurement intervals which have been preset (i.e., the interval during which the subject's state is closest to his basal metabolic state).

First, when the current clock time according to watch circuit 208 indicates that it is time to begin measurements, CPU 201 continuously inputs a body motion signal from body motion detector 101 via body motion sensor interface 209. In this embodiment, the initial value of measurement start time S and measurement end time E are set to 2:00 and 6:00, respectively, and have been stored in ROM 202 in advance. This is because, in the case of a healthy person, the sedate state reached during the time period from 2:00 to 6:00 when active metabolism declines the most is known as the daily change in body temperature, blood pressure, pulse rate, and the like.

Based on the body motion signal input during the measurement interval, CPU 201 detects the time at which the subject's acceleration is below the threshold value, and the time at which the acceleration first exceeds the threshold value after the aforementioned time, and specifies the time interval enclosed by these two points as the deep sleep interval.

Next, during the specified deep sleep interval, CPU 201 inputs the body temperature signal from body temperature detector 121 at specific time intervals via temperature sensor interface 211, and writes the obtained body temperature in RAM 203 in association with the input times. In parallel with this operation, CPU 201 determines the pulse rate by inputting the pulse wave signal from pulse wave detector 111 during the specified deep sleep interval at specific time intervals via pressure sensor interface 210, and stores these in association with the input times in RAM 203.

It is acceptable to create an association between the input time and the address of RAM 203 in advance, and then write the various data in the address corresponding to the input time, or to express data other than that initially measured in the form of a difference from the immediately preceding data. As a result, it is possible to reduce the amount of data stored in RAM 203.

When the deep sleep interval is not sufficiently long, i.e., when the deep sleep interval does not satisfy the duration required for the sedate period, then CPU 201 erases the data written in RAM 203 during the aforementioned deep sleep interval, and continues processing to detect a deep sleep interval.

Next, when the current time as detected by watch circuit 208 reaches the time at which measurements are to be concluded, then CPU 201 determines the curve from the body temperatures stored in RAM 203. Second, CPU 201 determines the inflection points which are minimums from among the inflection points along the curve. Third, when these inflection points are within the deep sleep interval, then CPU 201 specifies a specific time period centered around the clock time (measured clock time) of the inflection point as the sedate period, and reads out the pulse rate corresponding to this time as a standard value from RAM 203. In this case, it is also acceptable to obtain as the standard value an average value for the pulse rate obtained during the specified sedate period. In this way, the pulse rate when the subject is in (or near) his basal metabolic state is obtained.

CPU 201 corrects the information of the regression formula stored in RAM 201 in accordance with a method described above, based on the pulse rate which serves as the standard value and on the subject's basal metabolism (see FIG. 10B).

When it is not possible to specify a sufficiently long deep sleep interval, when the inflection point at which the minimal value was obtained was not within the deep sleep interval, or when a sedate period could not be specified because an inflection point where there was a minimum vale could not be obtained, then it is preferable to provide a design in which CPU 201 provides notice of that fact on display 205, and does not carry out correction of the regression formula information.

2-7-1: Calculation of calorie expenditure

The specific operation for using a calorie expenditure measuring device to calculate calorie expenditure will now be explained. This calculation operation is carried out by executing interrupt processing (1) shown in FIG. 17 at unit time intervals (fixed time intervals of one minute, for example). Interrupt processing (1) is executed by CPU 201 based on the interrupt signal from watch circuit 208.

First, at step Sa1, CPU 201 inputs the pulse wave signal from pulse wave detector 111 via pressure sensor interface 210, and determines the pulse rate.

Next, in step Sa2, CPU 201 inputs the body motion signal from body motion detector 101 via body motion sensor interface 209, and decides whether or not the subject is in an active state by determining the presence or absence of body motion.

If the subject is in a resting state, then in step Sa3, CPU 201 determines whether or not the pulse rate obtained above exceeded the threshold value. If the pulse rate exceeds the threshold value, then, in step Sa4, CPU 201 inputs the body temperature signal from body temperature detector 111 via temperature sensor interface 211, and determines whether or not the subject's body temperature exceeds the threshold value.

If the result of the determination in step Sa2 is "YES", then this corresponds to case (1) above. If the result of the determination in step Sa4 is "YES", then this corresponds to case (2) above. Accordingly, in step Sa5, CPU 201 selects the "active" regression formula.

On the other hand, if the result of the determination in step Sa3 is "NO", then this corresponds to case (4) noted above. If the result of the determination in step Sa4 is "NO", this corresponds to case (3) above. Accordingly, in step Sa6, CPU 201 selects a "resting" regression formula.

Next, in step Sa7, CPU 201 determines the oxygen intake quantity by substituting the pulse rate determined previously into the selected regression formula, multiplying this by a coefficient, and calculating the calorie expenditure per unit time. In step Sa8, CPU 201 provides notice of the calculated calorie expenditure on display 205 and stores the data in a time series in RAM 203.

Accordingly, by carrying out this type of interrupt processing (1), the calorie expenditure per unit time is displayed and updated at unit time intervals on display 205. At the same time, the value of the calorie expenditure per unit time interval is sequentially stored in a time series in RAM 203.

2-7-2: Change over time in calorie expenditure, comparison with target value

Next, the operation for carrying out processing during the specific time interval, for the values of calorie expenditure per unit time which are stored in RAM 203, will be explained. The specific time interval referred to here is equivalent to or longer than the interval of time during which interrupt processing (1) is carried out, and may be based on such usual time increment as minutes, hours, days, weeks, months or years. It is preferable to provide a design which enables selection from among these using switches Sw1 or Sw2.

This processing operation is carried out by executing interrupt processing (2) shown in FIG. 18 at specific time intervals. As in the case of interrupt processing (1), interrupt processing (2) is carried out by CPU 201 based on the interrupt signal from time circuit 208.

First, in step Sb1, CPU 201 reads out all the calorie expenditure values stored in RAM 203 from the last time interrupt processing (2) was activated through the present activation of interrupt processing (2), and adds all these values. In other words, during the specific time interval which is the period of interrupt processing (2), all of the calorie expenditure values which were determined at each unit time according to the execution of interrupt processing (1) described above are added, and the calorie expenditure during the specific time interval is calculated. If "hour" is selected as the specific time interval, then the calorie expenditure during one hour is calculated, while if "day" is selected, then the calorie expenditure during one day is calculated.

Next, in step Sb2, CPU 201 provides notice of the summed calorie expenditure on display 205, and, in step Sb3, stores the summed calorie expenditure value in a time series in RAM 203. The notification in step Sb2 is, for example, by means of a numerical display of the calorie expenditure. However, a variety of other arrangements might be considered.

In step Sb4, CPU 201 reads out the stored summed values for calorie expenditure over the past 30 minutes, for example. In step Sb5, CPU 201 carries out control so that a 2-dimensional display is realized on display 205 by sequentially plotting the read-out summed values on the y-axis and the recorded time interval on the x-axis. An example of the display on display 205 in this case is shown in FIG. 19. As shown in this figure, it is clear how calorie expenditure transitions during the specific time interval. Thus, this is beneficial to the subject as an indicator for subsequent exercise. Note that the specific interval of time in the example in this figure is "day".

Next, in step Sb6, CPU 201 determines whether or not the target value for calorie expenditure during the specific period of time has been set in RAM 203. This target value is, for example, set by the subject or a third party such as a physician by means of switch Sw1 or Sw2 or through communication with an external device.

When the results of this determination are "NO", then the following processing is not necessary, and CPU 201 concludes the current interrupt processing (2).

On the other hand, when the result of this determination is "YES", then CPU 201 compares the summed value from step Sb1 and the target value, and calculates the achievement rate G with respect to the target value from the following formula.

Achievement rate G=(summed value/target value)×100

Next, in step Sb8, CPU 201 displays the numerical value of the achievement rate G on display 207. In addition to a simple numerical display, however, a bar graph such as shown in FIG. 20 or a pie chart such as shown in FIG. 21 is also possible. Note that in the case of a bar graph or pie chart, the target value is indicated by means of the mark "▽", so that the relationship between the target and the calorie expenditure which has been summed at the current point in time may be understood at a glance. The specific time interval is "one day" in the examples shown in FIGS. 20 and 21. In addition, as shown in FIG. 22, a face chart may also be displayed in response to the achievement rate G.

After notification, CPU 201 should carry out the next processing, and end the current interrupt processing (2).

By executing interrupt processing (2), the summed value of calorie expenditure during the specific time interval is displayed and renewed on display 205 at each specific time interval. In addition, the change over time in this value is also displayed. If a target value is set, then the subject is notified of the achievement rate G with respect to the target value, or by a face chart corresponding thereto.

The preceding is the result of combining interrupt processing (1) and (2). However the same effect can be achieved by combining the following interrupt processing (3) and (4).
2-7-3: Calculation of calorie expenditure, subtraction from target value Interrupt processing (3) is executed at each unit time interval, and, in the same manner an interrupt processing (1), the calorie expenditure is calculated at this time. However, interrupt processing (3) differs from interrupt processing (1) in that it does not sequentially store the calorie expenditure, but subtracts this value from the target value for the specific time interval. Accordingly, it is possible to calculate the achievement rate G with respect to the target value from the start of interrupt processing (3) through the elapse of the specific time interval by examining the result of the subtraction operation. This calculation is carried out by executing interrupt processing (4) at the specific time interval.

An explanation of interrupt processing (3) will now be made with reference to FIG. 23. First, in step Sc1, CPU 201 determines whether or not a target value for calorie expenditure during a specific time period has been set in RAM 203. This target value is, for example, set by the subject or a third party such as a physician by means of switch Sw1 or Sw2 or through communication with an external device.

When the results of this determination are "NO", then the following processing is not necessary, and CPU 201 promptly concludes the current interrupt processing (3).

On the other hand, when the result of this determination is "YES", then, in step Sc2, CPU 201 determines whether or not the value of register n is zero. Register n is cleared to zero when interrupt processing (4) is carried out, and is incremented by "1" each time interrupt processing (3) is executed. Accordingly, when register n is zero, this indicates that interrupt processing (3) is being carried out for the first time since the previous interrupt processing (4) was executed.

If the result of this determination is "YES", then, in step Sc3, CPU 201 sets the target value in register TEMP, or skips Sc3 if the result of this determination is "NO".

Steps Sc4~Sc10 are equivalent to steps Sa1~Sa7 in interrupt processing (1). In other words, CPU 201 selects the regression formula which should be used after taking into consideration the subject's resting/active state, and psychological state, and calculates the value B for calorie expenditure per unit time.

When calculating value B, CPU 201 subtracts value B from register TEMP in step Sc11. The result of this subtraction operation is set as the new register TEMP value. In step Sc12, the subject is notified of the value of register TEMP which was the result of this subtraction operation via display 205.

Accompanying execution of the current interrupt processing (3), CPU 201 increments the value of register n by "1", and concludes processing.

Thus, when interrupt processing (3) is carried out for the first time since the execution of the previous interrupt processing (4), the target value is set in register TEMP. Subsequently, interrupt processing (1) is repeatedly carried out at each unit time interval, with the calorie expenditure subtracted from the register TEMP, and the subject notified of the results of this subtraction operation. Accordingly, the calorie expenditure is subtracted from the target value each time interrupt processing (1) is carried out.
2-7-4: Comparison with target value Interrupt processing (4) will now be explained with reference to FIG. 24. Interrupt processing (4) is executed at specific time intervals, with its significance being equivalent to as that of interrupt processing (2).

First, in step Sd1, CPU 201 compares the target value with the value in register TEMP currently, and calculates achievement rate G with respect to the target value using the following formula.

Achievement rate G=(target value−TEMP/target value)×100

Next, in step Sd2, CPU 201 displays the numerical value of the achievement rate G on display 207. In this case, a display based on numerical values such as shown in FIGS. 20 and 21, or a face chart such as shown in FIG. 22 may also be displayed in response to the achievement rate G.

Accompanying the execution of interrupt processing (4), in step Sd3, CPU 201 clears the value in register n to zero, and provides it to interrupt processing (3) which will be executed immediately thereafter.

As in the case of interrupt processing (1) and (2), by carrying out interrupt processing (3) and (4) in this way, it is possible to know the achievement rate G of the calories actually used with respect to the target value for calorie expenditure during the specific time interval.

2-7-5: Notification of the rate of change

In the above-described interrupt processing (2) and (4), the achievement rate G for the calories actually expended was determined with respect to a target value for calorie expenditure during a specific time interval. Here, for example, when the specific time interval is assumed to be comparatively short, such as 10 minutes, then, provided that the extent of change compared to the value 10 minutes before, i.e., the rate of change during the time interval, is known, it is possible to intuitively know the degree of activity which is necessary to reach the goal by setting the characteristics of the change over time as the desired goal.

This rate of change is calculated by reading out from RAM 203 the calorie expenditure which was calculated prior to the specific time interval, and then dividing the change between this calorie expenditure and the current calculated calorie expenditure by a time period corresponding to the specific time interval. It is acceptable to notify the subject of the calculated rate of change on display 205. In this case, the subject or a third party such as a physician sets a target value for the rate of change in RAM 203. On the other hand, when actually calculating the rate of change, it is acceptable to provide a design in which notice is provided by calculating the achievement rate G with respect to the target value. In addition, the calculated rate of change may be stored in RAM 203 in a time series.

2-7-6: Communication function

Next, an explanation will be made of the operation in the case where the calorie expenditure measuring device according the present embodiment carries out the sending and receiving of a variety of information through communication with the external device shown in FIG. 9.

When carrying out communication with the external device, the subject directs the LED and phototransistor of device main body 300 shown in FIG. 3 toward the communications window 606 of the external device.

The transmission function for sending information to the external device and the receiving function for receiving information from the external device will be explained separately.

2-7-6-1: Transmission function

The LED and phototransistor of device main body 300 are exposed and are directed opposite the communications window 606 of the external device. In this state, the subject operates switch Sw2 and sets the device in the mode for carrying out the transmission function. Then, CPU 201 in FIG. 2 sends the following information to device main body 600 via I/O interface 209 and the optical interface of the external device. In other words, CPU 201 sends the calorie expenditure at each unit time interval stored in a time series in step Sa8 of interrupt processing (1), the summed value for calorie expenditure during the specific time interval stored in a time series in step Sb3 of interrupt processing (2), or the rate of change in the calorie expenditure which is stored in a time series. In this case, it is also acceptable to provide a design in which the body motion detected by the body motion detector 101 means, the body temperature detected by the body temperature detector 101, and the pulse rate calculated by pulse rate calculator 114 are stored in RAM 203 in a time series, with these values being suitably selected and sent to the external device. An IrDA (Infrared Data Association) method may be used as an optical communications protocol in this case.

Transmission is thereby carried out from device main body 300, so that not only the subject, but also a third party such as a coach or physician is able to objectively know how calorie expenditure by the subject is changing. In addition, storage and analysis of this information is possible as a result.

The information sent by device main body 300 is processed at the external device side. As a result, it becomes unnecessary to carry out processing for notification of the change in calorie expenditure over time in step Sb5 or the achievement rate G at the device main body 300 side. As a result of this design, the processing load which must be carried out by device main body 300 can be reduced.

2-7-6-2: Receiving function

A target value for calorie expenditure during a specific time interval is set in the external device as a result of analysis by the subject or a third party such as a physician of the subject's calorie expenditure. It is also acceptable to set a target value for the rate of change in calorie expenditure during the specific time interval.

The LED and phototransistor of device main body 300 are directed opposite the communications window 606 of the external device. In this state, the subject operates switch Sw2 and sets the device in the mode for executing the receiving function. Then, the CPU 201 in FIG. 2 sends a signal indicating a data request to the external device, via I/O interface 207 and the optical interface of the external device. After receiving the signal, main body 600 of the external device sends information which will become the set target value, via the optical interface of the external device and I/O interface 207.

When the information which will become the target value is received at the device main body 300 side, then CPU 201 stores the received information in RAM 203, and sets the information as the target value in steps Sb6, Sc1, etc.

It is also acceptable to set the target value so that it changes over time. In this case, the target values which correspond to the execution times are used for the target values in steps Sb6, Sc1, etc.

By means of the calorie expenditure measuring device according to the present embodiment, it is possible to calculate the calorie expenditure per unit time with excellent accuracy, since a suitable regression formula is selected after taking into consideration each of the resting/active states of the subject, as well as his psychological state. The subject's basal metabolic state is specified, the regression formula is corrected in response to this, and the monthly or annual changes in the subject's physiological state are taken into consideration. As a result, it is possible to obtain a more accurate determination of calorie expenditure. For this reason, the calorie expenditure measuring device according to the present embodiment is extremely useful in the management of health.

In addition, as a result of the calorie expenditure measuring device according to the present invention, it is possible to known the calorie expenditure per unit time, as well as the change in calorie expenditure over time and the success ratio with respect to the target value for a specific time interval, making the device useful to the subject.

2-8: Deep body temperature and processed result thereof

In addition to being employed in the calculation of calorie expenditure, the body temperature which is sufficiently close to the subject's deep body temperature that is measured in this embodiment is also extremely significant from the perspective of clinical medicine. Further, since body temperature is measured using a device which is carried about portably by the subject, the present embodiment does not present a hindrance to the subject's daily activities and therefore represents an improvement over the previous art.

An explanation will now be made of the case where the subject or a third party is notified of the obtained deep body temperature and the result following processing thereof.

In this case, the subject selects the function for measuring body temperature by depressing switch Sw2, and indicates the start of body temperature measurement by pressing switch Sw1.

Then, first, in the same manner as when calculating the calorie expenditure, CPU 201 in FIG. 2 recognizes the depression of the aforementioned switch via a switch interface 204. Second, CPU 201 sequentially reads out the pulse wave signals from pressure sensors Ps1~Ps6 via pressure sensor interface 210, and stores these in RAM 203. Third, CPU 201 selects the largest value from among the six measured pressure values, and specifies the pressure sensor which measured this maximum pulse pressure. Then, CPU 201 sets the device so that measurements are carried out using the specified pressure sensor and its paired temperature sensor. Here, it is pressure sensor Ps3 which has detected the maximum pulse pressure from among pressure sensors Ps1~Ps6. When the measured value of the maximum pulse pressure exceeds a specific value, then at this time CPU 201 carries out control so that notification that a pulse is being detected is provided to display 205. This notification may be carried out by means of a letter display such as "detecting pulse". Alternatively, a "○" may be displayed to indicate detection is being carried out, while an "x" may be displayed to indicate that detection of the pulse is not being performed. As a result of this notification, it is possible for the subject to know that the body temperature measurement is being correctly carried out.

Next, CPU 201 carries out settings so that an interrupt is generated at specific time intervals (every 10 minutes, for example) with respect to watch circuit 208. Thereafter, when the interrupt is generated, CPU 201 takes up via temperature sensor interface 211 the measured temperature value at temperature sensor Ts3 which is disposed near pressure sensor Ps3, i.e., CPU 201 takes up the digital signal which expresses a body temperature which is sufficiently close to deep body temperature. The current time taken up from watch circuit 208 and the aforementioned measured temperature value are then stored as a pair in RAM 203. CPU 201 displays the current measured temperature value as the current body temperature on display 205.

Subsequently, each time an interrupt is generated by watch circuit 208, CPU 201 repeats the operations to display the measured temperature value at temperature sensor Ts3 on display 205 and store this measured temperature value and the time of measurement together as a pair in RAM 203.

When the subject wants to know the change in body temperature over time, he may depress switch Sw2 to select that function. As a result, CPU 201 reads out from RAM 203 the measured temperature values and the time of measurement for a specific portion of time from the current time, and, if needed, interpolates between each of the measured points using a suitable interpolation method. The data is then converted to display data and sent to display 205. As a result, a graph such as shown in FIG. 37 is displayed on display 205. In the figure, time [hours] is plotted along the horizontal axis, while temperature [° C.] is along the vertical axis.

When it is no longer necessary to measure body temperature, the subject again presses switch Sw1, and CPU 201 concludes the processing to measure body temperature by releasing the settings in watch circuit 208.

Note that in this design, it is also acceptable to send the measured temperature value and the time of measurement which constitute a pair recorded in RAM 203 to device main body 600 shown in FIG. 9. As a result, it becomes possible for not only the subject, but also a third party such as a coach or physician to objectively know how the deep body temperature of the subject has changed. Further, the storage and analysis of this information is also possible.

It is also acceptable to provide a design which displays the results of the derivative of body temperature with respect to time. If these results are displayed, it becomes possible to know the trend, etc. of the change in body condition.

In the case of this design, the device is formed so as to carry out measurements using a portable device such as a wristwatch, with the position of the artery automatically detected. As a result, there is no burden on the subject, and the measurement of a body temperature which is sufficiently close to deep body temperature can be carried out continuously. Accordingly, the device is useful in the management of health.

By realizing an accuracy of measurement of, for example, 0.1 [° C.], it is possible to obtain a continuous measurement of body temperature, while the subject himself is able to know the cyclical change in body temperature. This is extremely useful when carrying out health management. Further, the subject is able to know his "quality of life" (QOL) level, and use this as a basis for carrying out appropriate lifestyle activities to improve his QOL.

Although body temperature measured in this way is obtained at the surface of the subject's body, the temperature is deemed to be sufficiently close to the deep body temperature as described above. Since factors such as the temperature of the external environment or the evaporation of sweat from the body surface do not readily have an effect on this measurement, the body temperature obtained in this way may be used as one useful index showing the subject's own state.

2-9: Physiological information for basal metabolic state, and results of processing thereof Physiological information at the basal metabolic state (or a state close to it) which is specified in this embodiment should be such standard values as the monthly or annual change in the subject's physiology, as described above. Accordingly, as in the case of the deep body temperature, this information is useful not only in the calculation of calorie expenditure, but is itself extremely significant. For example, if a standard value for physiological information is measured over a long period of time such as a month or a year, it is possible to always know the natural changes in body. Thus, this is useful in a physical exam or in managing body condition. Moreover, in the case of the device of the current embodiment, no hindrance is presented to the subject's daily activities.

In addition to the temperature sensor for measuring the subject's body temperature, a design is preferable in which a temperature sensor is provided for measuring the temperature of the external environment (environmental temperature) as an optional structural component of the device. The reason for measuring the environmental temperature in this way is so that the difference between the environmental temperature and the body temperature can be obtained as a comfort index, as this has some effect on the subject's psychological and physical state. It is also acceptable to provide a design which not only provides notification of the physiological state, but in which a suitable regression formula is selected when calculating calorie expenditure, as was explained above.

Notification of the physiological information at the basal metabolic state and the processed result thereof to the subject or a third party will now be explained.

First, physiological information in this embodiment includes such factors as body temperature, pulse rate and respiration. The method for calculating body temperature and pulse rate have already been explained, so that the method for calculating the respiration rate from the pulse wave signal from pulse wave detector 111 will be explained here.

In an electrocardiogram, the interval between the R wave of one heartbeat and the R wave of the next heartbeat is referred to as the RR interval. FIG. 38 shows heartbeat and the RR interval obtained from the waveform of this heartbeat in an electrocardiogram. As may be understood from this figure, an analysis of the measured results in an electrocardiogram reveals that the RR interval varies over time.

On the other hand, variation in blood pressure measured at the periphery such as the radius artery or the like, is defined as the variation in blood pressure at each beat from contraction to relaxation of the heart, and corresponds to variation in the RR interval in an electrocardiogram. By carrying out spectral analysis of variations in the blood pressure, it may be understood that the variations are composed of waves having a plurality of frequencies, as shown in FIG. 39A. These may be classified into the following three types of variation components.

1. HF (high frequency) component which is the variation coinciding with respiration
2. LF (low frequency) component which varies with a periodicity of around 10 seconds
3. Trend which varies with a frequency which is lower than the measurement limits In order to obtain the respiration rate, CPU 201 first inputs the pulse waveform from pulse waveform detector 111 over a specific time interval (for example, 30 to 60 sec), and stores these in RAM 203. Second, CPU 201 carries out peak detection processing on all the inputted pulse waveforms, and determines the time interval, i.e., the RR interval, between the peaks of two adjacent pulse waves. Third, each RR interval obtained is interpolated using an appropriate method (for example, 3rd order spline interpolation). Fourth, CPU 201 carries out spectral analysis by performing an FFT (fast Fourier transform) operation on the curved lined after interpolation. The spectrum obtained as a result is shown in FIG. 39B. CPU 201 determines the maximum values in the spectrum and the frequencies corresponding to these maximum values, sets the maximum value obtained in the high frequency region to the HF component, and obtains the respiration rate from the frequency of the HF component. In the examples shown in FIG. 39A and 39B, the frequency near 0.25 Hz is the HF component, so that the respiration rate per minute is 0.25×60=15 times. Since the RR interval is the period of the pulse beat, CPU 201 can obtain the inverse of the RR interval as the pulse rate.

Next, when providing notification of physiological information at the basal metabolic state, the following modes are envisioned in the present embodiment. Namely, there is provided a "standard value measuring mode" for measuring and recording each of the standard values of pulse rate, respiration rate, and body temperature, a "standard value display mode" for providing notification of the standard values stored in the standard value measuring mode, and a "current value measuring mode" which measures the current pulse rate, respiration rate and body temperature, and notifies the subject of these results.

2-9-1: Operation of standard value measuring mode

In the standard value mode, CPU 201 specifies the deep sleep interval as explained in section $2\text{-}6_{-1}$ above, determines the pulse rate, body temperature, and respiration rate at specific time intervals by means of the methods described above, and writes this information into RAM 203 in association with the time of input.

Then CPU 201 specifies a sedate period as explained in section 2-6-1 above, and determines the standard values for this period, and writes them into RAM 203 in association with the date and time of input.

Accordingly, when the deep sleep interval and sedate period are specified, then the standard values for pulse rate, body temperature, and respiration rate, i.e., the physiological information when the subject is in (or close to) the basal metabolic state, are stored in RAM 203.

Note that in this design as well, it is acceptable to transmit the physiological information, which has been associated with a date and time of input in RAM 203, to device main body 600 shown in FIG. 9. In this way, it is possible for not only the subject, but also a third party such as a physician or coach, to objectively know how each of these basic values varies in the subject. Further, storage and analysis of this information is also possible. In the case of the following discussion, the various types of processing will be carried out in a device main body 300 which has the structure of a wristwatch.

2-9-2: Operation of standard value display mode

In the standard value display mode, notice of information related to the standard values measured in the standard value measuring mode is displayed on display 205 in response to the operational details input via switches Sw1 and Sw2.

For example, when a directive is given to display recent standard values, then, based on the current date and time of measurement, CPU 201 reads out recent standard values, the temperature of the surrounding environment at the time of measurement, and the time of the measurement, from RAM 203, and displays these on display 205. An example of the display shown on display 205 in this case is shown in FIG. 40. In the example shown in this figure, the [45], [15] and [36.3] shown in area $205_1$ are the standard values for pulse rate, respiration rate, and body temperature, respectively, while [22], [12/17], and [4:08] are the temperature of the surrounding environment at the time of measurement, the date of the measurement, and the time of the measurement, respectively. This enables the subject to know the time of the sedate period during the most recent day on which measurements where conducted (the current day, for example), each of the standard values for the pulse rate, respiration rate, and body temperature, and the temperature of the surrounding environment at the time when each of the standard values were measured.

In the case of this display, when the maximum and minimum values which are associated with the read out standard values are recorded in RAM 203, CPU 201 directs a flashing display of the numbers indicating the standard values (pulse rate, respiration) which are associated with the maximum and minimum values. It is of course acceptable to carry out notification using a method other than a flashing display. Thus, it is possible for the subject to know whether or not his physiological state while sedate is abnormal, or whether or not the threshold value T which is employed when specifying a deep sleep interval is suitable.

CPU 201 reads out past standard values from prior to the previous day and the temperature of the surrounding environment when the measurements were taken from RAM 203, and displays on display 205 the change over time through the present day in each of the standard values and the temperature of the surrounding environment when the measurements were made. In the example shown in FIG. 40, this change is displayed as a dashed line graph in area $205_2$. The line graph linking the "○" symbols is the standard value for the pulse rate, the line graph linking the "□" symbols is the standard value for respiration, the line graph linking the "Δ" is the standard value for body temperature, and the line graph linking the "x" expresses the change in the temperature of the environment when the measurements were made. The time increments noted in the horizontal direction in the figure may be selected in units of one week, one month, or one year, according to the specific operations carried out by the subject.

By displaying each of the standard values in the form of a graph in this way, it becomes possible for the subject to estimate his own biorhythms, and to discover when a deviation from these rhythms has occurred. Further, by studying the biorhythms for the day on which the deviation occurred, the subject will be able to adjust his biorhythms so that a deviation does not occur.

When a specific operation is generated from switch Sw1 and Sw2, CPU 201 converts the standard values measured on the most recent day prior to the previous day to a graph, and displays the graph in area $205_2$ which is disposed in the same way as the display in area $205_1$. In other words, the data from the current day and past data from before the previous day are displayed in contrast. When a specific operation is carried out in this state, CPU 201 switches the data displayed in area $205_2$ in order from the data of the previous day, the data from the previous week, the data of the previous month, and the data of the previous year. When data for the corresponding day is absent, then data from the day (excluding the current day) which is closest to that day is displayed (in the case where there is more than one day which is closest to the day which is lacking data, then any of these days may be used). As a result, the subject is able to correctly know the amount of change in the standard values.

2-9-3: Operation of the current value measuring mode

In the current value measuring mode, CPU 201 measures the current pulse rate, respiration, body temperature, and the temperature of the surrounding environment. The results of this measurement are displayed in area $205_1$ or $205_2$. CPU 201 switches the area in which display is conducted in response to operations by the subject. Here, when displaying each of the current standard values in area $205_2$, the subject is able to compare the standard values for the current day, which are displayed in area $205_1$. Thus, it is possible for the subject to know the degree of daily change based on his own physiological state.

As explained above, in this embodiment, by notifying the subject of physiological information for the basal metabolic state, the subject is able to know the fundamental quantity of his own activity. Moreover, since the device is in the form of a wristwatch, it can of course be worn during the day, but also at night without applying a burden on the subject. Thus, measurement of the standard values described above is easily accomplished. Further, since past standard values are recorded in RAM 203, confirmation of these values is always possible.

Since the temperature of the surrounding environment when the measurements are made is recorded and displayed in association with each of the standard values, the relationship between these can be understood by the subject. Once proficient, it is possible for the subject to accurately know the physiological state when sedate by referring to the measured values (standard values) for pulse and respiration after taking into consideration the difference between body temperature and the temperature of the surrounding environment. Note that it is also acceptable that in the standard value measuring mode and the standard value display mode, CPU 201 determine the aforementioned difference, and display this difference along with the standard values in the standard value display mode, thereby reducing the burden on the subject.

Note that management of body condition may be carried out on a daily basis by using each of the obtained standard values as standard data for the amount of activity. For example, as shown in FIG. 42, the heart rate (pulse rate) rises as the environmental temperature increases. There is almost no difference between individuals with respect to the breadth of this increase. Accordingly, if the standard data for the amount of activity and the environmental temperature at the time the measurements were made is obtained, then it is possible to specify the ideal pulse rate at an optional environmental temperature. If this ideal pulse rate is then compared with the actual pulse rate, it is possible to determine the quality of body condition. However, since the standard data for the amount of activity changes with the passage of days, it is possible for an error to be made when determining the quality of the body condition by assuming this value to be fixed. Thus, if the standard value of the pulse rate (and the environmental temperature when the measurements were made) obtained in this embodiment is used as standard data for the amount of activity, it is possible to accurately determine the quality of the body condition by taking into account the change in the data as days go by.

Similarly, this is also applicable in the case where determining the quality of body condition by monitoring the pulse rate when varying the load on the subject.

3: Example Applications and Modifications of the Present Embodiment

The following example applications and modifications are possible in the case of the above-described embodiment.

3-1: Example application and modification with respect to structure

The preceding embodiment employed a design where calorie expenditure was calculated directly from the pulse rate and the presence or absence of body motion. However, it is also acceptable to provide a design in which information such as pulse rate and the presence or absence of body motion are stored in RAM 203 in a time series, and this information is read out on the following day to calculate the calorie expenditure. A design is also possible in which this information is relayed to an external device, where the calorie expenditure is then calculated. In any case, by means of the structure shown in FIG. 1, the calorie expenditure is calculated by calculating the pulse rate and the presence or absence of body motion which are read out from RAM.

The preceding embodiment employed two regression formulas, one for when the subject is at rest and one for when the subject is active. However, the present invention is not limited thereto. Rather, a design may be provided in which the characteristics of the curved line shown in FIG. 10A are approximated by means of three or more regression formulas, with the applicable regression formula selected in response to body temperature, body motion, and pulse rate. Moreover, the present invention is not limited to a linear regression formula. Rather, it is also acceptable to provide a design in which the curved line is approximated using an exponential function or an nth order function, or a design in which a plurality of these approaches is employed.

In the preceding embodiment, 6 pairs of temperature and pressure sensors were employed, with the position at which a maximum pulse pressure could be measured selected, and body temperature measured at this site. This, however, is just one example, and it is of course acceptable to increase or decrease the number of pairs of temperature and pressure sensors. At one extreme is the device shown in FIG. 25, for example, in which just one pressure sensor and pulse sensor each are employed. As shown in this figure, in this design, fastener 302 is attached in a freely sliding manner to band 301, with pressure sensor Ps and temperature sensor Ts, which comprise one pair, formed in a unitary manner to fastener 302.

As shown in FIG. 26, when using this device, device main body 300 is wrapped around the left arm of the subject. Device main body 300 is fixed in place at a position where the maximum pulse pressure can be obtained by moving fastener 302 in a trial and error manner, so that pressure sensor Ps and temperature sensor Ts (which cannot be seen in FIG. 26 since they are positioned on the skin surface) which are provided to fastener 302 are positioned in the vicinity of radial artery TM.

On the other hand, if the number of sensor pairs is increased, then the range of measurement of pressure is extended and the accuracy of the disposed sensors can be increased. Thus, it is possible to obtain a more accurate measurement of body temperature.

While the pulse waveform can of course be obtained using pressure sensor Ps, the use of pressure sensor Ps in the preceding embodiment is really for the purpose of measuring the deep body temperature. In other words, pressure sensor Ps was employed because it is necessary to specify a position near an artery and measure the temperature at that position.

Accordingly, it is also acceptable to detect the pulse waveform by some means other than pressure sensor Ps. For example, a design may be considered in which the pulse waveform is detected by means of the pulse wave detector 111 shown in FIG. 27A. In this figure, pulse wave detector 111 has a sensor 320 which is formed of a blue LED and a light receiving element, and is blocked from light by sensor fixing band 321. As shown in FIG. 27B, pulse wave detector 111 is attached between the base and second joint of the subject's left index finger. Light is emitted from the blue LED. A portion of this light is reflected by the hemoglobin in the blood and is received at the phototransistor. The output of this received light is supplied to device main body 300 as a pulse wave signal, via cable 501.

When employing pulse wave detector 111 in this way, a connector 303 is provided at the 6 o'clock position on device main body 300. A connector piece 304 is provided to one end of cable 501 in a freely detachable manner. In this way, pulse wave detector 111 is not attached when employing the device as an ordinary wristwatch.

An InGaN-type (indium-gallium-nitrogen) blue LED is suitably employed for the blue LED which makes up pulse wave detector 111. The generated light spectrum of a blue LED has a peak at 450 nm, for example, with the generated light wavelength region being in the range of 350 to 600 nm. In this case, a GaAsP-type (gallium-arsenic-phosphorous) phototransistor may be used for the light receiving element corresponding to an LED having the light emitting characteristics described above. The wavelength region of the received light of the phototransistor has, for example, a main sensitive region in the range of 300 to 600 nm, with a sensitive region also present below 300 nm. When a blue LED and a phototransistor such as described above are combined, the pulse wave is detected in the overlapping wavelength region of 300 to 600 nm.

In the case of outside light, it tends to be difficult for light having a wavelength region of 700 nm or less to pass through the tissues of the finger. For this reason, even if the portion of the finger not covered by sensor-fixing band 321 is irradiated with outside light, the light does not reach the phototransistor through the finger tissue. Rather, only light in the wavelength region which does not influence the detection reaches the phototransistor. On the other hand, light in the low wavelength region of 300 nm or less is almost entirely absorbed by the skin surface. Thus, even if the wavelength region of the received light is set to 700 nm or less, the actual wavelength region of the received light is 300 to 700 nm.

Accordingly, it is possible to restrain the impact of outside light, without having to significantly cover the finger. Moreover, the absorption coefficient of blood hemoglobin with respect to light having a wavelength of 300 to 700 nm is large, and is several to 100-fold greater than the absorption coefficient with respect to light having a wavelength of 880 nm. Accordingly, as in this example, when light in the wavelength region (300 to 700 nm) in which the absorption characteristics are large is employed as the detection light, to match the absorption characteristics of hemoglobin, then the detected value varies with good sensitivity in response to changes in the blood volume. Accordingly, it is possible to increase the S/N ratio of the pulse wave signal which is based on the change in blood volume.

Further, it is also acceptable not to provide a body motion detector 101 or the like, but rather to obtain the intensity of body motion based on the pulse waveform detected by pulse wave detector 111. For further explanation, FIG. 41 shows an example of the frequency spectrum of the pulse waveform when the subject swings his arms with a fixed stroke. In this figure, S1 is the fundamental wave of body motion (stroke), S2 is the second higher harmonic wave of body motion, and M1 is the fundamental wave of the movement of blood through the arteries. As is clear from this figure, FFT or other frequency analysis processing is carried out on the pulse waveform. The frequency component accompanying body motion (body motion component) and the frequency component accompanying pulse (pulse wave component) are obtained from the results of this analysis. Accordingly, for the results of this frequency analysis, frequency components excluding the pulse wave components are defined as the body motion component. By studying the level of the body motion component, it is possible to obtain the intensity of body motion. In other words, it is possible to realize a step to determine whether or not body motion is present without employing a body motion detector 101, or the like. Of course, if the level of the body motion component is detectable, then it is also possible to use a frequency analysis method other than FFT.

In addition, the present embodiment measured the pulse rate, respiration, body temperature and temperature of the surrounding environment in the deep sleep interval during which the acceleration level was below a threshold value T. However, it is also acceptable to measure the pulse rate, respiration, body temperature, temperature of the surrounding environment, and the acceleration, and then sequentially determine the deep sleep interval and the sedate period after the measurement interval is finished.

Although the site of measurement in the preceding embodiments was in the vicinity of the radial artery, the present invention is not limited thereto. Rather, in addition to the area around the carotid artery, any site is acceptable provided that it is one at which the pulse can be detected at a position on the skin close to an artery. In addition to sites above the radius and on the neck, other areas may be considered including the hip joint or a site near the arteries of the upper arm, as shown in FIG. 31. More specifically, examples include the temporal artery, internal carotid artery, brachial artery, femoral artery, arteries at the rear of the neck, arteries at the back of the foot, and the like. Pressure sensor Ps and temperature sensor Ts are attached to these sites using adhesive tape, or are fixed in place by means of a band or supporter.

3-2: Calculation of pulse rate employing wavelet conversion

The preceding embodiments employed a structure in which the pulse rate was determined by carrying out FFT conversion of the pulse wave signal. The present invention is not limited thereto, however. For example, it is also possible to use the results of analysis of the pulse wave signal after carrying out wavelet conversion, i.e., to use the pulse wave data of each frequency region.

An explanation will now be made of the structure for carrying out wavelet conversion of the pulse wave signal obtained from the pressure sensor and phototransistor, and obtaining the pulse rate from the results of this analysis. This structure may be realized by substituting the FFT processor shown in FIG. 1 with the structure shown in FIG. 28.

In FIG. 28, wavelet converter 700 carries out conventional wavelet conversion with respect to the pulse wave signal MH which is output from pulse wave detector 111, and generates pulse wave analysis data MKD.

In general, in time frequency analysis in which the signal is simultaneously analyzed in both the time and frequency domains, the wavelet forms are the unit by which the signal part is extracted. Wavelet transformation shows the size of the each part of the signal extracted as these units. As the base function for defining wavelet transformation, a function $\psi(x)$ which has been localized with respect to both time and frequency is introduced as the mother wavelet. Here, wavelet transformation employing the mother wavelet $\psi(x)$ of a function f(x) is defined as follows.

$$(W_\psi f)(b, a) = \int_{-\infty}^{\infty} \frac{1}{\sqrt{a}} \psi\left(\frac{x-b}{a}\right) f(x) dx \quad (1)$$

In equation (1), b is the parameter employed when translating the mother wavelet $\psi(x)$, while a is the parameter used when scaling. Accordingly, wavelet $\psi((x-b)/a)$ in equation (1) is the wavelet obtained when transitioning mother wavelet $\psi(x)$ by b only, and scaling it by a only. Since the width of the mother wavelet $\psi(x)$ is extended in correspondence to the scale parameter a, 1/a corresponds to the frequency.

Frequency corrector 800 carries out frequency correction on pulse wave analysis data MKD. When comparing data from different frequency regions, it is necessary to correct for the effect of the term $[1/a^{1/2}]$ corresponding to frequency in the preceding equation (1). Frequency corrector 800 is provided for this purpose. Namely, frequency corrector 800 generates corrected pulse wave data MKD' by multiplying wavelet data WD by a coefficient $a^{1/2}$. As a result, it is possible to carry out correction based on each of the corresponding frequencies, so that the power density per frequency becomes constant.

Next, the detailed structure of wavelet converter 700 will be explained. FIG. 29 is a block diagram of wavelet converter 700.

In this figure, wavelet converter 700 carries out the processing for the calculation of equation (1) above, and has the following essential elements. Namely, wavelet converter 700 consists of a base function recorder W1 which records the mother wavelet $\psi(x)$; a scale converter W2 which converts scale parameter a; buffer memory W3; parallel translator W4 which carries out translation; and multiplier W5. Please note that various types of wavelets may be suitably employed for mother wavelet $\psi(x)$ which is stored in base function recorder W1, including Gabor wavelet, Mexican hat wavelet, Harr wavelet, Meyer wavelet, Shannon wavelet and the like.

When a mother wavelet $\psi(x)$ is read out from base function recorder W1, conversion of scale parameter a is carried out by scale converter W2. Scale parameter a corresponds to period, thus, the bigger a is, the more the mother wavelet extends above the time axis. In this case, the quantity of data for mother wavelet $\psi(x)$ recorded in base function recorder W1 is fixed, so that when a gets larger, the amount of data per unit time decreases. Scale converter W2 carries out interpolation to correct this, and generates a function $\psi(x/a)$ by performing weeding out processing when a gets smaller. This data is stored once in buffer memory W3.

Next, parallel translator W4 reads out function $\psi(x/a)$ from buffer memory W3 at a timing in response to translation parameter b, carrying out the parallel transition of function $\psi(x/a)$, to generate a function $\psi(x-b/a)$.

Next, multiplier W5 multiplies variable $1/a^{1/2}$, function $\psi(x-b/a)$ and the pulse wave signal obtained following A/D conversion, to generate pulse wave analysis data MKD. In this example, the pulse wave signal undergoes wavelet conversion. In this example, the pulse wave analysis data MDK is segregated into the frequency regions 0 Hz~0.5 Hz, 0.5 Hz~1.0 Hz, 1.0 Hz~1.5 Hz, 1.5 Hz~2.0 Hz, 2.0 Hz~2.5 Hz, 2.5 Hz~3.0 Hz, 3.0 Hz~3.5 Hz, and 3.5 Hz~4.0 Hz, and output.

Correction of this pulse wave analysis data MKD is carried out by frequency corrector 800, and supplied to pulse rate calculator 114 shown in FIG. 1 as corrected pulse wave data MKD'.

The processing cycle is carried out at an interval which is sufficiently higher, 8-fold for example, than the pulse rate which is typically assumed. In this case, the corrected pulse wave data MKD' which is generated at each heart beat becomes data M11~M88, shown in FIG. 30B.

Next, an explanation will be made of the case where pulse rate calculator 114 determines the pulse rate from corrected pulse wave data MKD'. When examining the pulse components of a typical pulse waveform, a sharp rise may be noted in each beat. For this reason, data indicating the high frequency components in this rising portion become large. Accordingly, first, pulse rate calculator 114 specifies the changing portion of the high frequency component, third, determines the interval of this portion, i.e., the interval of the beat, and third, calculates the inverse of this interval as the pulse rate.

For example, if corrected pulse wave data MKD' is a value such as shown in FIG. 30C, then the value of data M18 corresponding to this rising portion becomes larger than the values of the other data, such as [10]. The pulse interval is judged to be from the time until the next such value is detected, with the pulse rate then determined by taking the inverse of the pulse interval.

3-3: Other examples of the embodiments

The preceding embodiments employed a wristwatch structure for the calorie expenditure measuring device, however, the present invention is not limited thereto. A number of examples for the arrangement of the calorie expenditure measuring device according to the present invention will now be explained.

3-3-1: Necklace model

The calorie expenditure measuring device according to the present invention may be rendered in the form of a necklace such as shown in FIG. 32.

In this figure, pressure sensor Ps and temperature sensor Ts are provided to the end of a cable 31, and are attached to the area of the carotid artery by means of an adhesive tape 39, such as shown in FIG. 33. In FIG. 32, essential components of the device may be incorporated into a case 32 which is in the form of a broach which is hollow inside. The above-described display 205, switch Sw1 and switch Sw2 are provided to the front surface of this broach. One end of cable 31 is embedded in chain 33, with pressure sensor Ps and temperature sensor Ts electrically connected to pressure sensor interface 210 and temperature sensor interface 211 which are housed in case 32.

3-3-2: Eyeglasses

The calorie expenditure measuring device according to the present invention may also be incorporated into a pair of eyeglasses such as shown in FIG. 34.

As shown in the figures, the main body of the device in this embodiment is separated into a case 41a and a case 41b, which are attached to the stems 42 of the eyeglasses, respectively, and are connected electrically via a lead wire embedded in stems 42. A liquid crystal panel 44 is attached over the entire surface of the lens 43 side of case 41a. A mirror 45 is fixed to the edge of this lateral surface at a specific angle. A drive circuit for liquid crystal panel 44 which includes a light source (not shown) and a circuit for forming the display data are incorporated in case 41a. These form display 205 shown in FIGS. 2 or 3. The light emitted from this light source passes via liquid crystal panel 44, and is reflected at mirror 45 to incident on lens 43 of the eyeglasses. The principle elements of the device are incorporated in case 41b, with switches Sw1 and Sw2 described above attached to the upper surface thereof. On the other hand, pressure sensor Ps and temperature sensor Ts are electrically connected to pressure sensor interface 210 and temperature sensor interface 211 which are housed in case 41b, via cable 31. Pressure sensor Ps and temperature sensor Ts are attached to the carotid artery in the same manner as in the case of the necklace. The lead wires which connect case 41a and case 41b may be designed so as to extend along stems 42. In this example, the device main body was divided into case 41a and case 41b, however, it is also acceptable to employ a case formed in a unitary manner. Mirror 45 may be moveable so that the user can adjust the angle between the liquid crystal panel 44 and mirror 45.

3-3-3: Card model

As another example of an embodiment of the present invention, the calorie expenditure measuring device may be rendered in the form of a card such as shown in FIG. 35. The device in this form is stored in the left breast pocket of the subject's shirt, for example. Pressure sensor Ps and temperature sensor Ts are electrically connected to pressure sensor interface 210 and temperature sensor interface 211 which are stored in a case, via cable 31. As in the case of the necklace, they are attached to the area of the carotid artery of the test subject.

3-3-4: Pedometer

As another embodiment of the present invention, the calorie expenditure measuring device may be incorporated into the pedometer shown in FIG. 36A, for example. The main body of this pedometer device is attached to the subject's waist belt 51 as shown in FIG. 36B. Pressure sensor Ps and temperature sensor Ts are electrically connected to pressure sensor interface 210 and temperature sensor interface 211 housed in a case, via cable 31. They are fixed in place to the area of the femoral artery at the subject's hip joint by means of adhesive tape, and are protected by supporter 52. In this case, it is preferable to sew cable 31 into the clothing, so that it does not present a hindrance to the subject's daily activities.

3-4: Arrangements for display and notification

The preceding embodiments employed a design in which the calculated results were all displayed on display 205; however, the present invention is not limited thereto. Namely, a variety of arrangements are possible for notification, which do not rely on the sense of sight. In this sense, notification in the present invention means a method which relies on any one of the five senses. For example, a design may be provided which relies on the sense of sound in which the subject is notified of the calculated calorie expenditure, achievement rate G, or rate of change by means of a synthesized voice. Similarly, a design is also possible which relies on the tactile sense by employing vibration in the notification.

We claim:

1. A body temperature measuring device, comprising:
   pulse wave detecting means for detecting over a specific area the pulse pressure around the site where the subject's pulse is present;
   temperature detecting means for detecting temperature which is provided near the pulse wave detecting means; and
   body temperature specifying means for specifying as the body temperature the temperature detected at the site at which the largest pulse pressure from among the pulse pressures detected in the specific area was detected.

2. A body temperature measuring device according to claim 1, further comprising a plurality of pairs of pulse wave detecting means and temperature detecting means,
   wherein the body temperature specifying means specifies as the body temperature the temperature detected by the temperature detecting means corresponding to the pulse wave detecting means which detected the largest pulse pressure as the body temperature.

3. A body temperature measuring device according to claim 2, wherein the plurality of pairs of pulse wave detecting means and temperature detecting means are disposed in rows at roughly a right angle with respect to the direction of elongation of the arterial vessels at which the detection of pulse pressure is carried out.

4. A body temperature measuring device according to claim 1 or claim 2, further comprising storing means for storing at fixed intervals of time the body temperature specified by the body temperature specifying means.

5. A body temperature measuring device according to claim 4, further comprising notifying means for notifying the subject of the change in body temperature over time, based on the body temperatures stored in the fifth storing means.

6. A body temperature measuring device according to claim 4, further comprising transmission means for transmitting the body temperature stored in the storing means to an external device.

7. A body temperature measuring device according to claim 1 or claim 2, further comprising:

pulse discriminating means which determines whether or not the pulse wave detecting means is detecting the pulse pressure; and notifying means which notifies the subject of the result of the determination by the pulse discriminating means.

8. A body temperature measuring device according to claim 1 or claim 2, further comprising a body motion detecting means for detecting the subject's body motion, wherein the body temperature specifying means specifies the body temperature when a determination is made that the body motion is within specified limits based on the detected results of the body motion detecting means.

9. A body temperature measuring device according to claim 1, further comprising:

basal metabolic state specifying means for specifying the subject's basal metabolic state from the body temperature specified by the body temperature specifying means;

physiological information measuring means for measuring the subject's physiological information;

physiological information specifying means for specifying the physiological information measured by the physiological information measuring means as the physiological information of the subject's basal metabolic state, in the case where the basal metabolic state was been specified by the basal metabolic state specifying means.

10. A body temperature measuring device according to claim 9, wherein the basal metabolic state specifying means specifies the minimum in the subject's body temperature as the basal metabolic state.

11. A body temperature measuring device according to claim 9, further comprising body motion detecting means for detecting the subject's body motion, wherein the basal metabolic state specifying means specifies the subject's basal metabolic state when body motion is with specific limits based on the results of detection by the body motion detecting means.

12. A body temperature measuring device according to claim 9, further comprising time keeping means for measuring the current time, wherein the basal metabolic state specifying means specifies the basal metabolic state in the case where the current time kept by the time keeping means is determined to be within a preset time period.

13. A body temperature measuring device according to claim 9, further comprising:

body motion detecting means for detecting the subject's body motion; and time keeping means for measuring the current time;

wherein the basal metabolic state specifying means specifies the basal metabolic state in the case where body motion is determined to be within specific limits based on the results of detection by the body motion detecting means, and the current time kept by the time keeping means is determined to be within a preset time period.

14. A body temperature measuring device according to claim 9, further comprising:

environmental temperature detecting means for detecting the temperature of the environment around the subject; and correcting means for correcting the physiological information measured by the physiological information measuring means based on the environmental temperature detected by the environmental temperature detecting means.

15. A body temperature measuring device according to claim 9 or claim 14, further comprising storing means for storing physiological information specified by the physiological information specifying means.

16. A body temperature measuring device according to claim 15, further comprising notifying means for notifying the subject of a change in the physiological information based on the stored results of the storing means.

17. A body temperature measuring device according to claim 16, wherein the notifying means carries out notification in response to the deviation between the physiological information measured by the physiological information measuring means and the physiological information stored in the sixth storing means.

18. A body temperature measuring device according to claim 15, further comprising transmitting means for transmitting the physiological information stored in the storing means to an external device.

19. A body temperature measuring device, comprising:

a plurality of pulse wave detectors each detecting at a respective site a corresponding pulse pressure of a subject;

a plurality of temperature detectors each detecting a temperature of the respective site corresponding to one of the plurality of the pulse wave detectors; and a body temperature detector selector to select a detected temperature detected by one of the plurality of temperature detectors corresponding to the respective site having the largest pulse pressure.

20. A body temperature measuring device according to claim 19, wherein the plurality of pulse detectors are arranged in a first row and the plurality of temperature detectors are arranged in a second row.

21. A body temperature measuring device according to claim 20, wherein the first and second rows are disposed in rows at roughly a right angle with respect to the direction of elongation of the arterial vessels at which the detection of pulse pressure is carried out.

22. A body temperature measuring device according to claim 19 or claim 20, further comprising a first memory to store at fixed intervals of time the detected temperature selected by the body temperature selector.

23. A body temperature measuring device according to claim 22, further comprising a notifier to notify the subject of a change in body temperature over time, based on the body temperatures stored in the first memory.

24. A body temperature measuring device according to claim 22, further comprising a transmitter to transmit the body temperature stored in the first memory to an external device.

25. A body temperature measuring device according to claim 19 or claim 20, further comprising:

a pulse discriminator which determines whether or not the plurality of pulse wave detectors are detecting the pulse pressure; and a notifier to notify the subject of the result of the determination by the pulse discriminator.

26. A body temperature measuring device according to claim 19 or claim 20, further comprising a body motion detector to detect the subject's body motion, wherein the body temperature selector selects the body temperature when a determination is made that the body motion is within specified limits based on the detected results of the body motion detector.

27. A body temperature measuring device according to claim 19, further comprising:

a basal metabolic state specifier to specify the subject's basal metabolic state from the body temperature specified by the body temperature selector;

a physiological information measurer to measure the subject's physiological information;

a physiological information specifier to specify the physiological information measured by the physiological information measurer as the physiological information of the subject's basal metabolic state, in the case where the basal metabolic state was been specified by the basal metabolic state specifier.

28. A body temperature measuring device according to claim 27, wherein the basal metabolic state specifier specifies the minimum in the subject's body temperature as the basal metabolic state.

29. A body temperature measuring device according to claim 27, further comprising a body motion detector to detect the subject's body motion, wherein the basal metabolic state specifier specifies the subject's basal metabolic state when body motion is with specific limits based on the results of detection by the body motion detector.

30. A body temperature measuring device according to claim 27, further comprising a timer to measure the current time, wherein the basal metabolic state specifier specifies the basal metabolic state in the case where the current time kept by the timer is determined to be within a preset time period.

31. A body temperature measuring device according to claim 27, further comprising:

a body motion detector to detect the subject's body motion; and a timer to measure the current time;

wherein the basal metabolic state specifier specifies the basal metabolic state in the case where body motion is determined to be within specific limits based on the results of detection by the body motion detector, and the current time kept by the timer is determined to be within a preset time period.

32. A body temperature measuring device according to claim 27, further comprising:

an environmental temperature detector to detect the temperature of the environment around the subject; and a corrector to correct the physiological information measured by the physiological information measurer based on the environmental temperature detected by the environmental temperature detector.

33. A body temperature measuring device according to claim 27 or claim 32, further comprising a memory to store physiological information specified by the physiological information specifier.

34. A body temperature measuring device according to claim 33, further comprising a notifier to notify the subject of a change in the physiological information based on the stored results of the memory.

35. A body temperature measuring device according to claim 34, wherein the notifier carries out notification in response to the deviation between the physiological information measured by the physiological information measurer and the physiological information stored in the memory.

36. A body temperature measuring device according to claim 33, comprising a transmitter to transmit the physiological information stored in the memory to an external device.

* * * * *